(12) United States Patent
DeFreitas et al.

(10) Patent No.: US 12,295,759 B2
(45) Date of Patent: *May 13, 2025

(54) HORIZONTALLY-DISPLACEABLE FOAM BREAST COMPRESSION PADDLE

(71) Applicant: Hologic, Inc., Marlborough, MA (US)

(72) Inventors: Kenneth DeFreitas, Patterson, NY (US); Jay A. Stein, Boston, MA (US); Alan Rego, Woodbury, CT (US)

(73) Assignee: Hologic, Inc., Marlborough, MA (US)

( * ) Notice: Subject to any disclaimer, the term of this patent is extended or adjusted under 35 U.S.C. 154(b) by 119 days.

This patent is subject to a terminal disclaimer.

(21) Appl. No.: 18/119,055

(22) Filed: Mar. 8, 2023

(65) Prior Publication Data

US 2023/0355190 A1 Nov. 9, 2023

Related U.S. Application Data

(63) Continuation of application No. 17/150,495, filed on Jan. 15, 2021, now Pat. No. 11,622,736.

(60) Provisional application No. 63/082,257, filed on Sep. 23, 2020, provisional application No. 62/965,511, filed on Jan. 24, 2020.

(51) Int. Cl.
| | |
|---|---|
| *G03C 5/16* | (2006.01) |
| *A61B 6/00* | (2006.01) |
| *A61B 6/04* | (2006.01) |
| *A61B 6/50* | (2024.01) |

(52) U.S. Cl.
CPC .......... *A61B 6/0414* (2013.01); *A61B 6/0487* (2020.08); *A61B 6/4476* (2013.01); *A61B 6/502* (2013.01)

(58) Field of Classification Search
CPC ... A61B 6/502; A61B 6/0407; A61B 10/0041; A61B 6/03; A61B 6/032; A61B 6/037; A61B 6/04; A61B 6/0414; A61B 6/0435; A61B 6/0485; A61B 2017/00796; A61B 90/17

See application file for complete search history.

(56) References Cited

U.S. PATENT DOCUMENTS

| | | |
|---|---|---|
| 3,578,971 A | 5/1971 | Lasky |
| 3,971,950 A | 7/1976 | Evans et al. |
| 4,496,557 A | 1/1985 | Malen |

(Continued)

FOREIGN PATENT DOCUMENTS

| | | |
|---|---|---|
| AU | 2008201638 | 5/2008 |
| CN | 1586399 | 3/2005 |

(Continued)

OTHER PUBLICATIONS

Digital Clinical Reports, Tomosynthesis (GE Brochure 98-5493, Nov. 1998), 8 pgs.

(Continued)

*Primary Examiner* — Don K Wong
(74) *Attorney, Agent, or Firm* — Merchant & Gould P.C.

(57) ABSTRACT

A breast compression paddle includes a bracket, a rigid substrate, and a foam compressive element. The bracket removably secures the breast compression paddle to an imaging system. The rigid substrate is secured to the bracket and includes a first edge and a second edge disposed opposite the first edge. The foam compressive element is slidably secured to the rigid substrate.

18 Claims, 27 Drawing Sheets

(56) References Cited

U.S. PATENT DOCUMENTS

| | | | |
|---|---|---|---|
| 4,567,899 A | 2/1986 | Kamens et al. |
| 4,943,986 A | 7/1990 | Barbarisi |
| 4,962,515 A | 10/1990 | Kopans |
| 5,040,198 A | 8/1991 | Hixson, Sr. |
| 5,051,904 A | 9/1991 | Griffith |
| 5,107,255 A | 4/1992 | Shiraishi |
| 5,109,398 A | 4/1992 | Hunt |
| 5,199,056 A | 3/1993 | Darrah |
| 5,257,121 A | 10/1993 | Steinberg |
| 5,359,637 A | 10/1994 | Webber |
| 5,398,272 A | 3/1995 | Bouscary et al. |
| 5,474,072 A | 12/1995 | Shmulewitz |
| 5,506,877 A | 4/1996 | Niklason |
| 5,553,111 A | 9/1996 | Moore et al. |
| D376,012 S | 11/1996 | Hixson, Sr. |
| 5,706,327 A | 1/1998 | Adamkowski |
| 6,049,583 A | 4/2000 | Galkin |
| 6,122,542 A | 9/2000 | Lee |
| 6,289,235 B1 | 9/2001 | Webber |
| 6,577,702 B1 | 6/2003 | Lebovic et al. |
| 6,587,578 B2 | 7/2003 | Godik et al. |
| 6,647,092 B2 | 11/2003 | Eberhard |
| 6,682,484 B1 | 1/2004 | Entrekin et al. |
| 6,765,984 B2 | 7/2004 | Higgins et al. |
| 6,850,590 B2 | 8/2005 | Galkin |
| 6,968,033 B2 | 11/2005 | Lebovic et al. |
| 6,974,255 B1 | 12/2005 | Hixson, Sr. |
| 6,975,701 B2 | 12/2005 | Galkin |
| 7,123,684 B2 | 10/2006 | Jing et al. |
| 7,203,348 B1 | 4/2007 | Karrsemeijer |
| 7,245,694 B2 | 7/2007 | Jing et al. |
| 7,319,735 B2 | 1/2008 | DeFreitas |
| 7,430,272 B2 | 9/2008 | Jing et al. |
| 7,489,761 B2 | 2/2009 | DeFreitas et al. |
| 7,505,555 B2 | 3/2009 | Hermann et al. |
| 7,512,211 B2 | 3/2009 | Galkin |
| 7,583,786 B2 | 9/2009 | Jing et al. |
| 7,634,049 B2 | 12/2009 | Galkin |
| 7,639,780 B2 | 12/2009 | Minyard |
| 7,656,993 B2 | 2/2010 | Hoernig |
| 7,702,142 B2 | 4/2010 | Ren et al. |
| 7,742,558 B2 | 6/2010 | Mertelmeier et al. |
| 7,760,853 B2 | 7/2010 | Jing et al. |
| 7,792,244 B2 | 9/2010 | DeFreitas et al. |
| 7,822,457 B2 | 10/2010 | Lokhandwalla et al. |
| 7,831,296 B2 | 11/2010 | Defreitas |
| 7,869,563 B2 | 1/2011 | Defreitas et al. |
| 8,155,421 B2 | 4/2012 | Ren et al. |
| 8,175,219 B2 | 5/2012 | DeFreitas et al. |
| 8,787,522 B2 | 7/2014 | Smith et al. |
| 9,050,009 B2 | 6/2015 | Den Heeten |
| 9,226,718 B1 | 1/2016 | Baxley |
| 9,332,947 B2 | 5/2016 | DeFreitas et al. |
| 9,498,180 B2 | 11/2016 | Ren et al. |
| 9,649,075 B2 | 5/2017 | DeFreitas et al. |
| 9,743,997 B2 | 8/2017 | Grimbergen |
| 9,782,135 B2 | 10/2017 | Stango et al. |
| 9,826,950 B2 | 11/2017 | Den Heeten |
| 10,603,002 B2 | 3/2020 | Stango |
| 10,888,292 B2 | 1/2021 | Stango |
| 11,259,759 B2 | 3/2022 | Stango et al. |
| 11,633,164 B2 | 4/2023 | Stango |
| 11,950,941 B2 | 4/2024 | Stango |
| 2001/0038861 A1 | 11/2001 | Hsu |
| 2002/0032373 A1 | 3/2002 | Godik et al. |
| 2002/0061090 A1 | 5/2002 | Lindstrom |
| 2003/0007597 A1* | 1/2003 | Higgins .............. A61B 6/0414 378/37 |
| 2003/0007598 A1 | 1/2003 | Wang et al. |
| 2003/0099325 A1 | 5/2003 | Galkin |
| 2003/0174807 A1 | 9/2003 | Lebovic |
| 2004/0066882 A1 | 4/2004 | Eberhard |
| 2004/0066884 A1 | 4/2004 | Claus |
| 2004/0066904 A1 | 4/2004 | Eberhard |
| 2004/0094167 A1 | 5/2004 | Brady |
| 2004/0156472 A1 | 8/2004 | Galkin |
| 2004/0218727 A1 | 11/2004 | Shoenfeld |
| 2005/0008117 A1 | 1/2005 | Livingston |
| 2005/0063509 A1 | 3/2005 | DeFreitas et al. |
| 2005/0113681 A1 | 5/2005 | DeFreitas et al. |
| 2005/0113683 A1 | 5/2005 | Lokhandwalla et al. |
| 2005/0113863 A1 | 5/2005 | Ramzipoor et al. |
| 2006/0050844 A1* | 3/2006 | Galkin .............. A61B 6/4283 378/37 |
| 2006/0165215 A1 | 7/2006 | Galkin |
| 2007/0081625 A1 | 4/2007 | Sendai |
| 2007/0223652 A1 | 9/2007 | Galkin |
| 2007/0242794 A1 | 10/2007 | Stanton |
| 2007/0280412 A1 | 12/2007 | Defreitas et al. |
| 2008/0043904 A1 | 2/2008 | Hoernig |
| 2008/0080668 A1 | 4/2008 | Kashiwagi |
| 2008/0087830 A1 | 4/2008 | Kashiwagi |
| 2008/0181361 A1 | 7/2008 | Eldered et al. |
| 2008/0240345 A1 | 10/2008 | Galkin |
| 2008/0242979 A1 | 10/2008 | Fischer et al. |
| 2008/0247508 A1 | 10/2008 | Harrington |
| 2009/0003519 A1 | 1/2009 | DeFreitas et al. |
| 2009/0135997 A1 | 5/2009 | DeFreitas |
| 2009/0175408 A1 | 7/2009 | Goodsitt et al. |
| 2009/0262887 A1 | 10/2009 | Iordache et al. |
| 2009/0268865 A1 | 10/2009 | Ren |
| 2009/0304146 A1 | 12/2009 | Ramsauer |
| 2009/0324049 A1 | 12/2009 | Kontos et al. |
| 2010/0046698 A1 | 2/2010 | Lebovic et al. |
| 2010/0049093 A1 | 2/2010 | Galkin |
| 2010/0111249 A1 | 5/2010 | Mertelmeir et al. |
| 2010/0329418 A1 | 12/2010 | Blevis |
| 2011/0058724 A1 | 3/2011 | Claus |
| 2011/0064190 A1 | 3/2011 | Ruimi |
| 2011/0087098 A1 | 4/2011 | Fischer et al. |
| 2011/0257919 A1 | 5/2011 | Reiner |
| 2012/0033868 A1 | 2/2012 | Ren |
| 2012/0051522 A1 | 3/2012 | Nishino |
| 2012/0114095 A1 | 5/2012 | Smith et al. |
| 2012/0150034 A1 | 6/2012 | DeFreitas |
| 2012/0277625 A1 | 11/2012 | Nakayama |
| 2013/0012837 A1 | 1/2013 | Krogure |
| 2013/0028499 A1 | 1/2013 | Tsujii |
| 2013/0051520 A1 | 2/2013 | Ramsauer |
| 2013/0129039 A1 | 5/2013 | DeFreitas et al. |
| 2013/0272493 A1 | 10/2013 | Otokuni |
| 2014/0107493 A1 | 4/2014 | Yuen |
| 2014/0296701 A1 | 10/2014 | Hancu et al. |
| 2014/0328458 A1 | 11/2014 | Erhard et al. |
| 2014/0378816 A1 | 12/2014 | Oh |
| 2015/0272682 A1 | 10/2015 | Sheng |
| 2015/0282770 A1 | 10/2015 | Klanian et al. |
| 2016/0066875 A1 | 3/2016 | Jacob et al. |
| 2016/0081633 A1 | 3/2016 | Stango et al. |
| 2016/0166234 A1 | 6/2016 | Zhang |
| 2016/0183889 A1 | 6/2016 | Matsuura |
| 2016/0242707 A1 | 8/2016 | Defreitas et al. |
| 2017/0055930 A1 | 3/2017 | Hagiwara |
| 2017/0251991 A1 | 9/2017 | Wang |
| 2017/0340303 A1 | 11/2017 | Stango |
| 2017/0347976 A1 | 12/2017 | DeFreitas et al. |
| 2018/0125437 A1 | 5/2018 | Stango et al. |
| 2018/0165840 A1 | 6/2018 | Bernard |
| 2018/0184999 A1 | 7/2018 | Davis |
| 2020/0069274 A1 | 3/2020 | Stango |
| 2020/0178926 A1 | 6/2020 | Kshirsagar |
| 2020/0196971 A1 | 6/2020 | Laviola |
| 2020/0359974 A1 | 11/2020 | DeFreitas |
| 2020/0359975 A1 | 11/2020 | Banks |
| 2020/0390405 A1 | 12/2020 | DeFreitas |
| 2021/0015435 A1 | 1/2021 | DeFreitas |
| 2021/0113169 A1 | 4/2021 | Stango |
| 2021/0228165 A1 | 7/2021 | Defreitas |
| 2022/0087627 A1 | 3/2022 | Stango |
| 2023/0233161 A1 | 7/2023 | DeFreitas |
| 2023/0346329 A1 | 11/2023 | Stango |

(56) References Cited

U.S. PATENT DOCUMENTS

| | | | |
|---|---|---|---|
| 2023/0363726 | A1 | 11/2023 | Banks |
| 2024/0245364 | A1 | 7/2024 | Stango |

FOREIGN PATENT DOCUMENTS

| | | |
|---|---|---|
| CN | 1738573 | 2/2006 |
| CN | 1810209 | 8/2006 |
| CN | 101766490 A | 7/2010 |
| CN | 102196772 | 9/2011 |
| CN | 102448375 | 5/2012 |
| CN | 102781328 | 11/2012 |
| CN | 103281961 | 9/2013 |
| CN | 104066374 | 9/2014 |
| CN | 105286904 | 2/2016 |
| CN | 105637562 | 6/2016 |
| CN | 105769236 | 7/2016 |
| CN | 107170031 | 9/2017 |
| CN | 107518908 | 12/2017 |
| CN | 109893158 | 6/2019 |
| CN | 211432963 | 9/2020 |
| CN | 112004473 | 11/2020 |
| CN | 115348838 | 11/2022 |
| EP | 955886 | 11/1999 |
| EP | 1004274 A1 | 5/2000 |
| EP | 2716228 | 4/2014 |
| EP | 2341832 B1 | 7/2014 |
| EP | 2943125 B1 | 9/2018 |
| GB | 2545641 | 6/2017 |
| JP | S53-103672 | 8/1978 |
| JP | H03-86154 | 4/1991 |
| JP | H05-076409 U | 3/1992 |
| JP | 2003-525681 | 9/2003 |
| JP | 2004-261306 | 9/2004 |
| JP | 2005-523043 | 8/2005 |
| JP | 2006-212427 | 8/2006 |
| JP | 2007-135704 | 6/2007 |
| JP | 2008-518722 A | 6/2008 |
| JP | 2009-526618 A | 7/2009 |
| JP | 2009-219656 | 10/2009 |
| JP | 8-215172 | 3/2010 |
| JP | 2011-072667 | 4/2011 |
| JP | 2011-206436 | 10/2011 |
| JP | 2011-206438 | 10/2011 |
| JP | 2011-206439 | 10/2011 |
| JP | 2011-212111 | 10/2011 |
| JP | 2011-224351 | 11/2011 |
| JP | 2011-250842 | 12/2011 |
| JP | 2012-125536 | 7/2012 |
| JP | 2012-170718 | 9/2012 |
| JP | 2012-228404 | 11/2012 |
| JP | 2013017491 | 1/2013 |
| JP | 2014-068884 | 4/2014 |
| JP | 2014-068885 | 4/2014 |
| JP | 2015-027382 | 2/2015 |
| JP | 2016-022061 | 2/2016 |
| JP | 2016-517740 | 6/2016 |
| KR | 10-2011-0089446 | 8/2011 |
| KR | 10-2014-0058066 | 5/2014 |
| NL | 2020910 B1 | 11/2019 |
| WO | 2004/030523 | 4/2004 |
| WO | 2006/050466 | 5/2006 |
| WO | 2010/028208 | 3/2010 |
| WO | 2010/102087 | 9/2010 |
| WO | 2011/058730 | 5/2011 |
| WO | 2014059366 | 4/2014 |
| WO | 2014/074602 | 5/2014 |
| WO | 2014/176445 | 10/2014 |
| WO | 2015/054518 | 4/2015 |
| WO | 2016/073445 | 5/2016 |
| WO | 2018/067005 | 4/2018 |
| WO | 2018/089118 | 5/2018 |
| WO | 2018/170265 | 9/2018 |
| WO | 2019/004821 | 1/2019 |
| WO | 2019/088826 | 5/2019 |
| WO | 2019/227042 | 11/2019 |
| WO | 2019/227044 | 11/2019 |
| WO | 2019/227051 | 11/2019 |
| WO | 20190227042 | 11/2019 |
| WO | 20190227044 | 11/2019 |

OTHER PUBLICATIONS

European Communication and Search Report in Application 18847121.3, mailed Apr. 8, 2021, 5 pages.
European Extended Search Report in Application 15857678.5, dated Jun. 26, 2018, 8 pages.
European Extended Search Report in Application 18843590.3, mailed Mar. 25, 2021, 9 pages.
European Extended Search Report in Application 18843788.3, mailed Mar. 29, 2021, 16 pages.
Grant, D.G., "Tomosynthesis: a three-dimensional imaging technique", IEEE Trans. Biomed. Engineering, vol. BME-19, #1, (Jan. 1972), pp. 20-28.
Japanese Rejection in Application 2019-521374, mailed Jul. 26, 2021, 5 pages.
PCT International Preliminary Report on Patentability in International Application PCT/IB2018/056208, mailed Feb. 27, 2020, 10 pages.
PCT International Preliminary Report on Patentability in International Application PCT/US2015/058782, dated May 18, 2017, 10 pgs.
PCT International Preliminary Report on Patentability in International Application PCT/US2017/053311, mailed May 14, 2019, 14 pgs.
PCT International Preliminary Report on Patentability in International Application PCT/US2018/046304, mailed Feb. 11, 2020, 14 pgs.
PCT International Preliminary Report on Patentability in International Application PCT/US2018/046312, mailed Feb. 11, 2020, 12 pgs.
PCT International Preliminary Report on Patentability in International Application PCT/US2021/013716, mailed Aug. 4, 2022, 14 pages.
PCT International Search Report and Written Opinion in International Application PCT/IB2018/056208, mailed Nov. 13, 2018, 12 pages.
PCT International Search Report and Written Opinion in International Application PCT/US2021/013716, mailed Jun. 28, 2021, 24 pages.
PCT International Search Report and Written Opinion of the International Searching Authority for corresponding International Patent Application No. PCT/US2015/058782 dated Feb. 17, 2016, 14 pgs.
PCT International Search Report and Written Opinion of the International Searching Authority for International Patent Application No. PCT/US2017/053311 mailed Mar. 6, 2018, 21 pages.
PCT International Search Report and Written Opinion of the International Searching Authority for International Patent Application No. PCT/US2018/046304 mailed Dec. 11, 2018, 18 pages.
PCT International Search Report and Written Opinion of the International Searching Authority for International Patent Application No. PCT/US2018/046312 mailed Dec. 11, 2018, 14 pages.
PCT Invitation to Pay additional Fees, in Application PCT/US2021/013716, mailed May 6, 2021, 17 pages.
U.S. Appl. No. 60/628,516 entitled "Matching geometry generation and display of mammograms and tomosynthesis images", filed Nov. 15, 2004, 20 pgs.

* cited by examiner

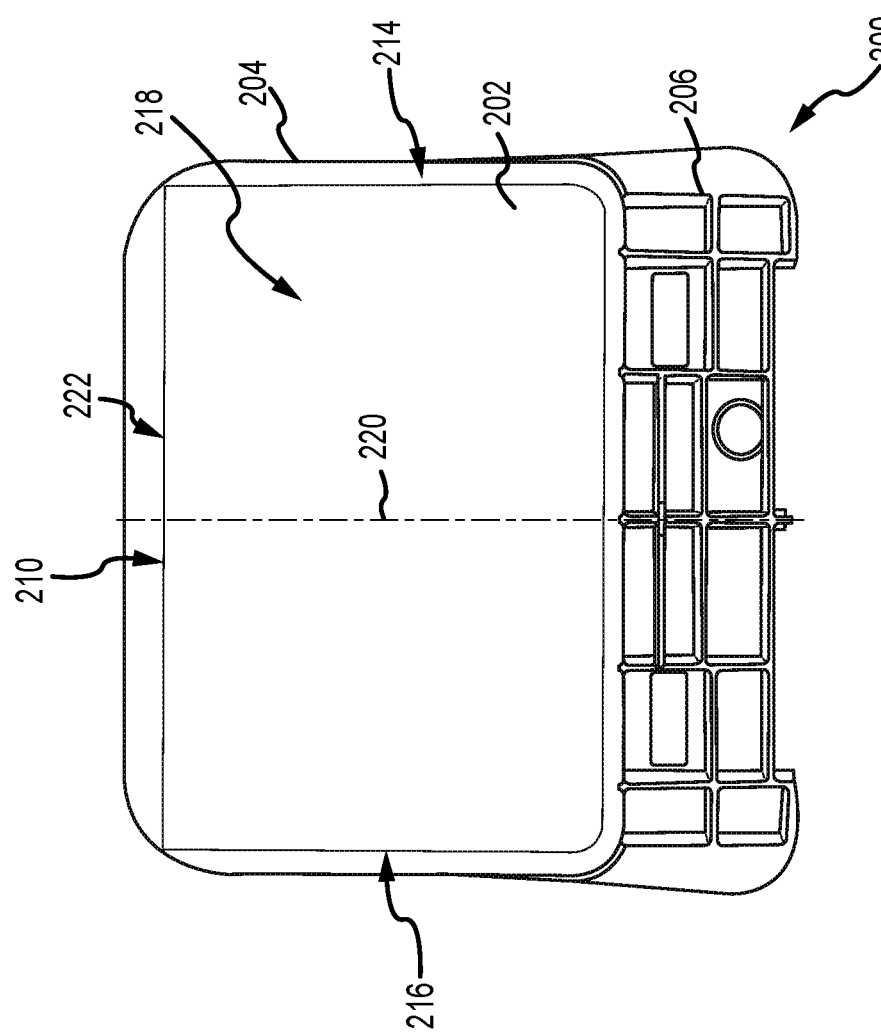

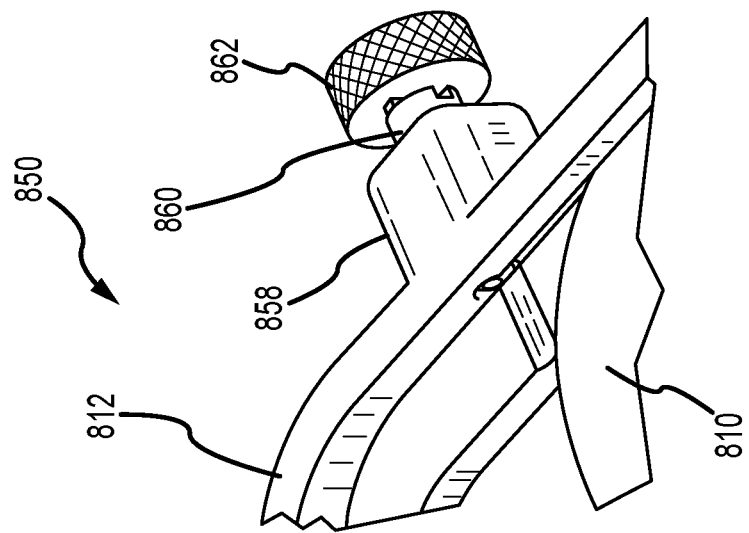
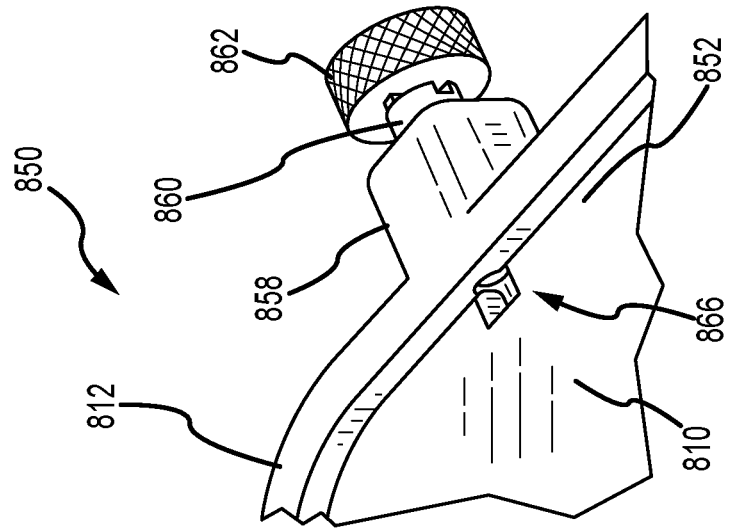
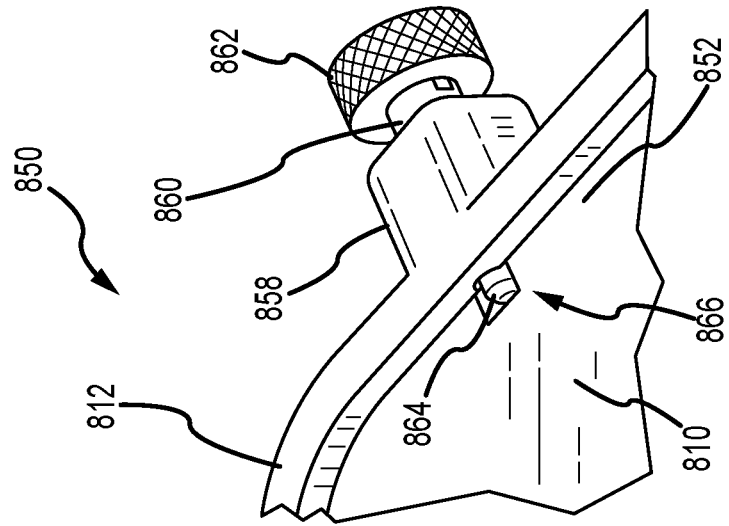

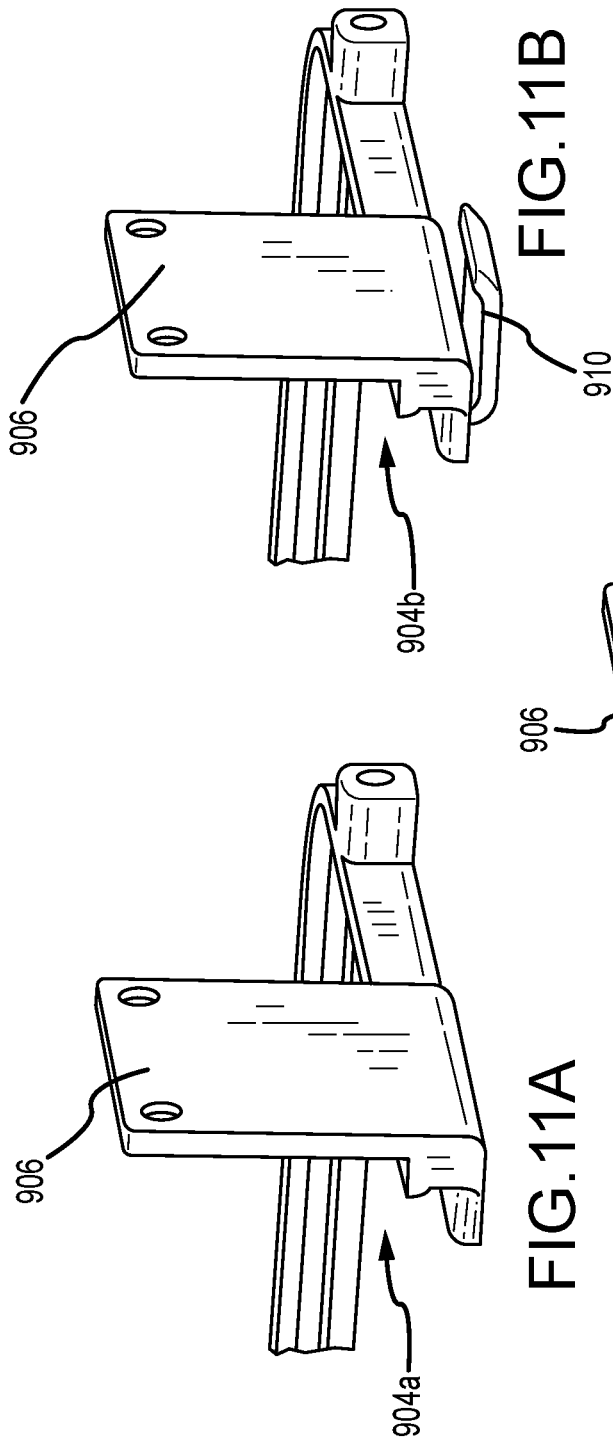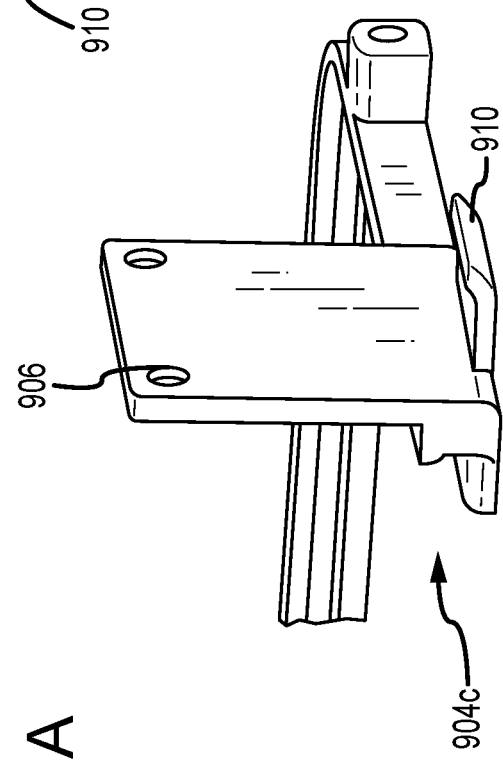

HORIZONTALLY-DISPLACEABLE FOAM BREAST COMPRESSION PADDLE

CROSS-REFERENCE TO RELATED APPLICATIONS

This application is a continuation of U.S. patent application Ser. No. 17/150,495, now U.S. Pat. No. 11,622,736, filed Jan. 15, 2021, which claims the benefit of priority to U.S. Provisional Application No. 63/082,257, filed Sep. 23, 2020; and U.S. Provisional Application No. 62/965,511, filed Jan. 24, 2020, the disclosures of which applications are hereby incorporated by reference herein in their entireties.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to a breast compression paddle including: a bracket for removably securing the breast compression paddle to an imaging system; a rigid substrate secured to the bracket, wherein the rigid substrate includes a first edge and a second edge disposed opposite the first edge; and a foam compressive element slidably secured to the rigid substrate. In an example, the paddle includes a rail system for slidably securing the foam compressive element to the rigid substrate. In another example, the rail system includes: a first rail secured to the first edge; a second rail secured to the second edge; a first collar slidably secured to the first rail; and a second collar slidably secured to the second rail, wherein the foam compressive element is secured relative to the first collar and the second collar. In yet another example, the paddle includes a bridge spanning the first collar and the second collar, and the foam compressive element is secured to the bridge. In still another example, the paddle includes a bridge substantially parallel to a bottom surface of the rigid substrate. In another example, the foam compressive element is positionable between a first position disposed below the rigid substrate and a second position disposed substantially below the bracket.

In another aspect, the technology relates to a breast imaging system including: an x-ray source; a breast support platform; a compression arm movably disposed between the x-ray source and the breast support platform; a rigid substrate; a rail system removably secured to at least one of the compression arm and the rigid substrate; and a foam compressive element secured to at least one of the rail system and the rigid substrate. In an example, the rigid substrate is removably secured to the rail system, and the foam compressive element is secured to the rigid substrate. In another example, the rail system includes a single rail and a carrier slidably engaged with the single rail, wherein the carrier is removably secured to a bracket secured to the rigid substrate. In yet another example, the rigid substrate is slidably secured to the rail system in a first position and a second position, wherein in the first position, the rigid substrate is substantially centered on the compression arm and in the second position, the rigid substrate is disposed substantially to a side of the compression arm. In still another example, the rigid substrate is secured to the compression arm at a bracket and removably secured to the rail system, and the foam compressive element is secured to the rail system. In an example, the rail system includes a bridge and the foam compressive element is secured to the bridge. In another example, the foam compressive element and the bridge are positionable in a first position substantially below the bracket and the compression arm and a second position substantially below the rigid substrate.

In another aspect, the technology relates to a method of positioning a breast of a patient for x-ray imaging, the method including: moving a rigid substrate towards the breast in a direction substantially orthogonal to a support platform supporting the breast; moving a foam compressive element in a direction substantially parallel to the support platform; and contacting the breast with the foam compressive element. In an example, moving the rigid substrate includes a first moving the rigid substrate operation and a second moving the rigid substrate operation, and wherein moving the foam compressive element is performed between the first moving the rigid substrate operation and the second moving the rigid substrate operation. In another example, the method includes placing the breast on the support platform. In yet another example, the direction substantially parallel to the support platform is substantially parallel to the chest wall. In still another example, the direction substantially parallel to the support platform is substantially orthogonal to the chest wall. In an example, moving the rigid substrate and moving the foam compressive element are each performed via at least one motor. In another example, moving the foam compressive element in the direction substantially parallel to the support platform includes moving the rigid substrate in the direction substantially parallel to the support platform.

In another aspect, the technology relates to a breast imaging system including: an x-ray source; a breast support platform; a compression arm movably disposed between the x-ray source and the breast support platform; a compression paddle secured to the compression arm, at least one of the breast support platform and the compression paddle define a compressive surface; and a foam compressive element secured to no more than about 30% of the compressive surface. In another aspect, the technology relates to a breast imaging system including: an x-ray source; a breast support platform, wherein the breast support platform includes a non-compressive edge; a compression arm movably disposed between the x-ray source and the breast support platform; a compression paddle secured to the compression arm; and a foam compressive element secured to the non-compressive edge. In an example, the foam compressive element comprises a coating.

In another aspect, the technology relates to a breast compression paddle including: a bracket for removably securing the breast compression paddle to an imaging system; a substrate receptacle movably secured to the bracket; a rigid substrate receivably secured to the substrate receptacle, wherein the rigid substrate includes a first edge and a second edge disposed opposite the first edge; and a foam compressive element secured to the rigid substrate. In an example, the breast compression paddle further includes a drive system disposed within the bracket; and a bearing mount secured to the rigid substrate and movably secured to the drive system, such that an actuation of the drive system moves the bearing mount and the rigid substrate from a first position to a second position. In another example, when in the first position, the rigid substrate is disposed substantially below a compressive region of the bracket and when in the second position, the rigid substrate is disposed substantially away from the compressive region of the bracket. In yet another example, when in the second position the first edge of the rigid substrate is disposed below the compressive region and the second edge is not disposed below the compressive region. In still another example, the rigid substrate includes a third edge and a fourth edge disposed opposite the third edge, wherein the third edge and the fourth edge are receivably secured to the substrate receptacle.

In another example of the above aspect, the substrate receptacle includes at least one locking pin. In an example, the rigid substrate includes a flange and wherein the foam compressive element is at least partially surrounded by the flange. In another example, the breast compression paddle further includes a cover covering the foam compressive element, wherein the covering is connected to the flange.

In another aspect, the technology relates to a compression paddle including: a rigid substrate; a foam compressive element secured to the substrate; and at least one magnet connected to the rigid substrate for magnetically engaging at least a portion of a breast imaging system.

BRIEF DESCRIPTION OF THE DRAWINGS

FIGS. 2A-2C are various views of a breast compression paddle having a foam compressive element.

FIGS. 9A-9F depicts various views of components of a connection system for connecting a foam compressive element to a compression paddle.

FIGS. 11A-11C depict examples of substrate receptacles.

DETAILED DESCRIPTION

Figure 1A:
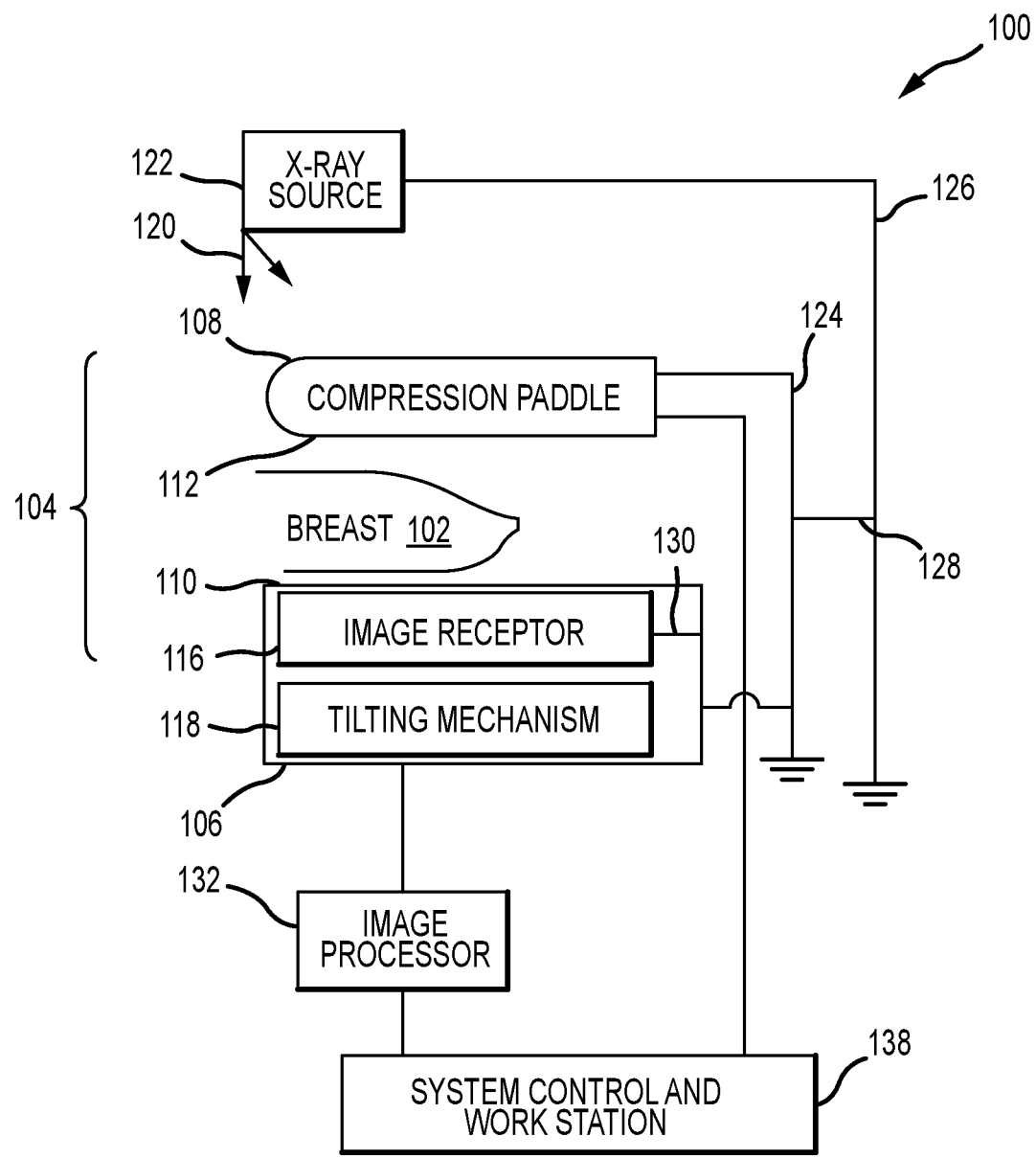
FIG. 1A is a schematic view of an exemplary imaging system.
Figure 1B:
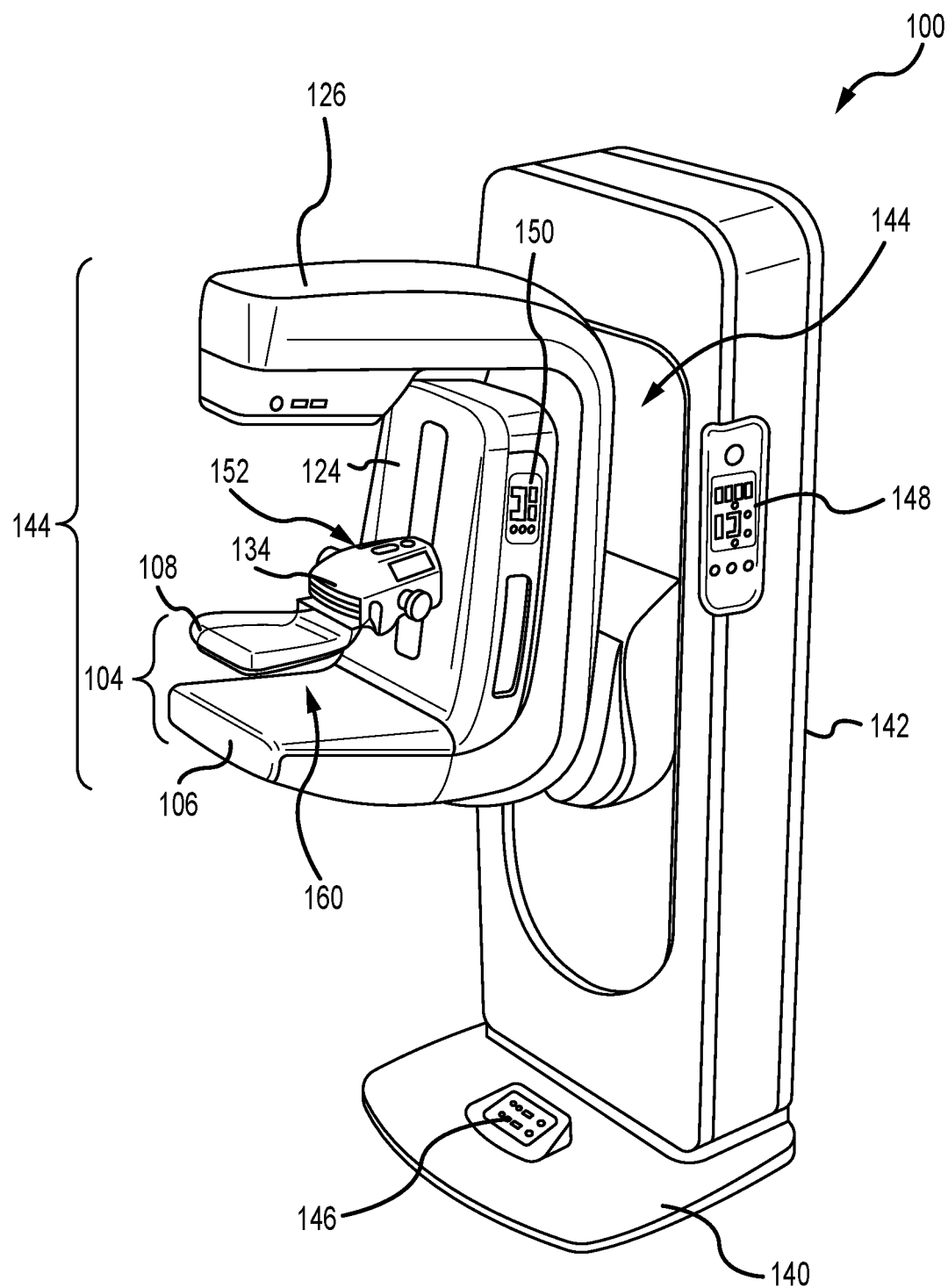
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography and tomosynthesis) via a breast compression immobilizer unit 104 that includes a static breast support platform 106 and a moveable paddle 108. Different paddles, each having different purposes, are known in the art. Certain examples paddles are also described herein for context. The breast support platform 106 and the paddle 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Either or both of these compression surfaces 110, 112 may be rigid plastic, a flexible plastic, a resilient foam, a mesh or screen, and so on. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

The imaging system 100 includes a floor mount or base 140 for supporting the imaging system 100 on a floor. A gantry 142 extends upwards from the floor mount 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 144.

A number of interfaces and display screens are disposed on the imaging system 100. These include a foot display screen 146, a gantry interface 148, a support arm interface 150, and a compression arm interface 152. In general the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

During imaging of a breast, it is often desirable to immobilize the breast through compression. For instance, by compressing the breast, the breast can be made thinner, thus requiring a lower dose of radiation. Further, by immobilizing the breast, image blurring from movement of the breast during imaging is reduced. Other benefits may also be realized by compressing the breast. However, a rigid breast compression paddles may cause discomfort to the patient whose breast is being compressed. One reason for discomfort that the patient may feel is that the compression force is non-uniformly distributed throughout the breast. It is often concentrated at the thickest portion of the breast, usually near the chest wall, at or near the lower front edge of the compression paddle and the upper front corner of the breast platform. The anterior portion of the breast, such as near the nipple, may receive less compressive force, or no compressive force. The paddle may not even contact this portion of the breast. (The terms front, lower, and upper pertain to using a craniocaudal (CC) imaging orientation, with the patient facing the front of the imaging system, although it should be understood that other imaging orientations, including mediolateral oblique (MLO), are used with the same equipment.)

To improve these issues, the compression systems described herein include a foam compressive element that is positioned below a lower surface of the rigid compressive paddle and contacts the breast during compression. Compression paddles utilizing foam compressive elements are described generally in PCT International Patent Application Nos. PCT/US2019/033998, PCT/US2019/034001, and PCT/US2019/034010, all filed May 24, 2019, the disclosures of which are hereby incorporated by reference herein in their entireties. Such paddles stabilize and compress the breast, while reducing discomfort associated with compression paddles having only rigid compressive surfaces.

The foam at least partially conforms in shape to the breast as the paddle is lowered and the foam compresses thus stabilizing the breast for imaging, without requiring the compression pressure typical in breast imaging systems. The foam can also be placed underneath the breast (e.g., secured to the breast support platform). Additionally, the foam may be placed on the portions of the compression paddle and breast platform that face the chest wall. As the compression paddle is lowered, the foam compresses and takes on a curved shaped that approximates the shape of the breast. However, unlike hard plastic compression paddles, compression forces need not be so high as to completely flatten the breast. Rather, the foams described herein are utilized to stabilize the breast, not necessarily to effectuate full compression, which is usually performed by flat rigid compression paddles (or by breast compression elements that have a very thin layer of foam disposed thereon. In a traditional mammogram system, since the breast is not flat, the appearance of the breast would differ (depending on the level of compression of the particular volume of interest), although this appearance may be corrected by image processing algorithms. For imaging systems such as tomosynthesis, however, the foam only appears in slices outside of the boundaries of the breast. For slices inside the breast, the structures blur out and are not visible. As such, the paddles utilizing foams described herein may be used for both mammography and tomosynthesis imaging, although some post-imaging processing may be required to realize all advantages thereof.

Figure 2A:
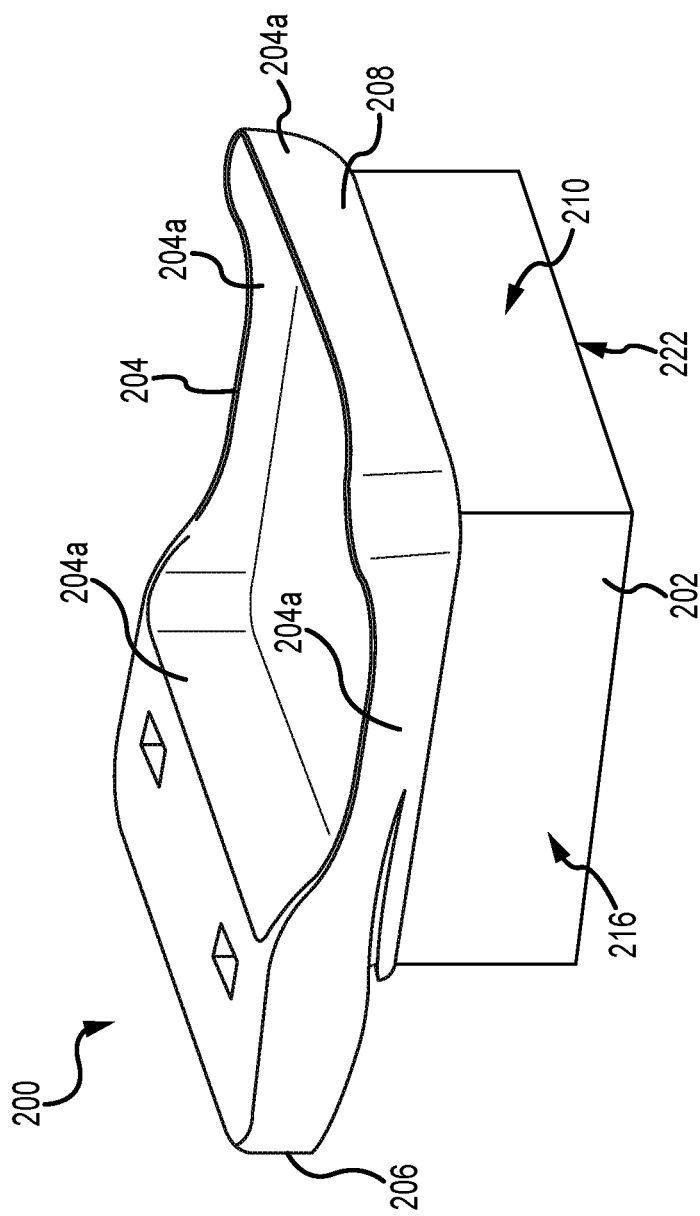
Figure 2B:
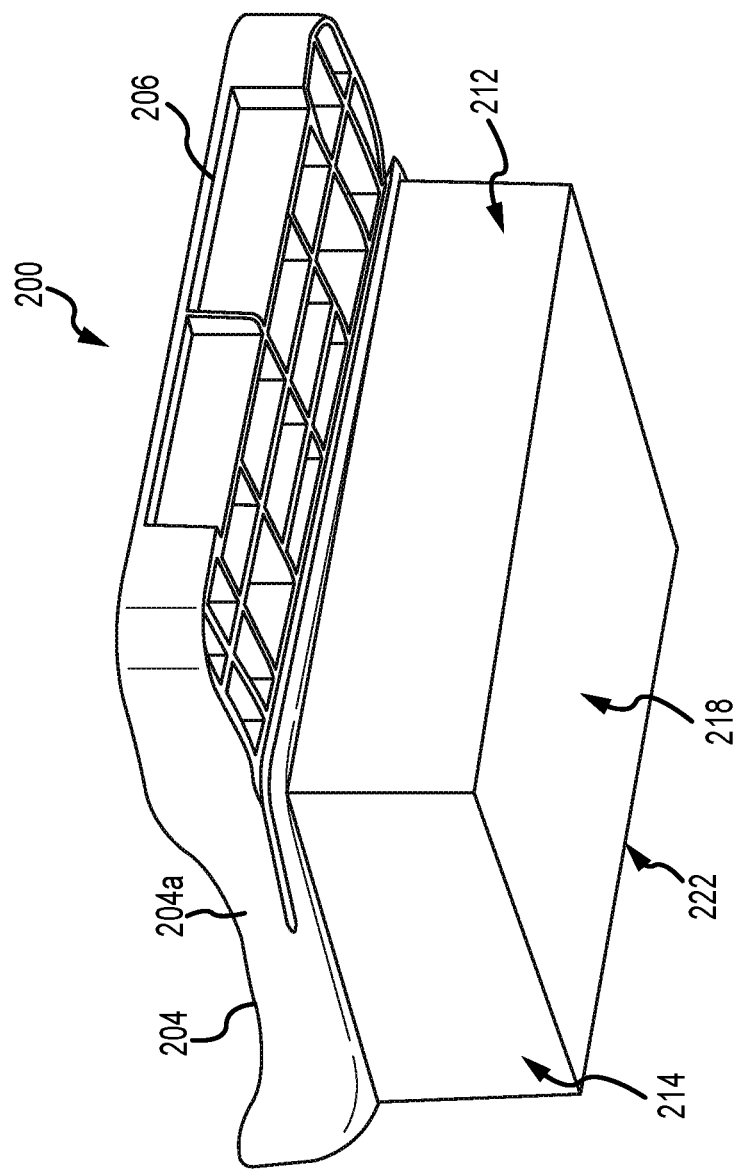

FIGS. 2A-2C are various views of a breast compression paddle 200 having a foam compressive element 202 secured to a rigid substrate 204. FIGS. 2A-2C are described concurrently. The paddle 200 includes a bracket portion 206, generally integral with the substrate 204 for connecting the paddle to compression arm of an imaging system. The bracket portion 206 is generally a reinforced portion of the paddle 200 and may be made of the same material as the rigid substrate 204. In examples, the bracket portion is formed integral with the rigid substrate 204. The paddle 200 also includes a leading face 208, opposite the bracket portion 206, which is disposed proximate a chest wall of a patient during compression and imaging procedures. In examples, the substrate may be rigid. As used herein, the term "rigid" does not imply that the substrate 204 is free from bending during compression of a breast, rather that the substrate 204 displays greater resistance to bending or deformation than the foam compressive element 202 secured to a bottom of the substrate 204. Raised walls 204a provide additional rigidity.

The foam compressive element 202 may be secured to a bottom surface of the substrate 204 with a chemical adhesive. In other example, an upper surface of the compressive element may be a rigid plastic or other material to which the foam compressive element 202 is secured. A plurality of bolts, hooks, or other mechanical fasteners (not shown) may be used to connect this rigid plastic to the rigid substrate 204 of the paddle 200. If such mechanical fasteners are used, it may be desirable to dispose said fasteners away from areas of the foam compressive material 202 that are expected to compress against a breast, so as to avoid pressure points and resulting discomfort associated therewith, as well as to prevent artifacts from appearing in any resulting x-ray images.

The foam compressive element 202 includes a number of edge surfaces. A leading edge surface 210 is disposed proximate the leading face 208 of the substrate 204 so as to be disposed proximate the chest wall of a patient during compression and imaging procedures. A trailing edge surface 212 is disposed opposite the leading edge surface 210, proximate the bracket portion 206. Lateral edge surfaces 214, 216 are also depicted. In general, these lateral edge surfaces 214, 216 may be depicted as inner or outer lateral edge surfaces, consistent with terminology typically used to describe inner and outer sides of the breast. Of course, a person of skill in the art will recognize that the same compression paddle 200 may be used to compress either breast, one at a time, which would effectively change the application of the terms "inner" and "outer" to the lateral edge surfaces of the foam compressive material 202. Further, a mid-plane 220 is disposed between the lateral edge surfaces 214, 216, at an approximate midpoint thereof. The mid-plane 220 is disposed substantially orthogonal to a compressive surface 218 that is disposed on an underside of the foam compressive material 202. Portions of the compressive surface 218 will contact the breast during compression. In another example, the foam compressive material 202 may be covered with a biocompatible cover, which may protect the foam compressive material 202 from absorbing bodily fluids. In examples, the may be disposable or cleanable. To improve the patient experience, the cover may be manufactured of a soft material where it contacts the patient. To prevent fluid transfer into the foam compressive material 202, an opposite plastic side may contact the foam compressive material 202. An interface 222 is located where the compressive surface 218 meets the leading edge surface 210. The shape of the interface 222 during compression aids in defining the foam compressive material 202 and the function thereof.

Since a thick foam compressive element decreases visibility of the breast during positioning, proper positioning the breast prior to compression may be effected. As such, the technologies described herein incorporate features that help increase visibility of the breast. Further, access to the breast may also be increased by using the technologies described herein. These include utilizing thick foam compressive elements that may move (e.g., horizontally) relative to the compression arm and/or the breast support platform of a breast imaging system. In such a case, the compression arm may be lowered towards the patient breast with greater breast visibility and access for the imaging technician. Once at a predetermined distance from the breast, the foam compressive element may be moved into a desired location appropriate for compression, then the compression arm may be further lowered until contact with the breast is made.

Figure 3A:
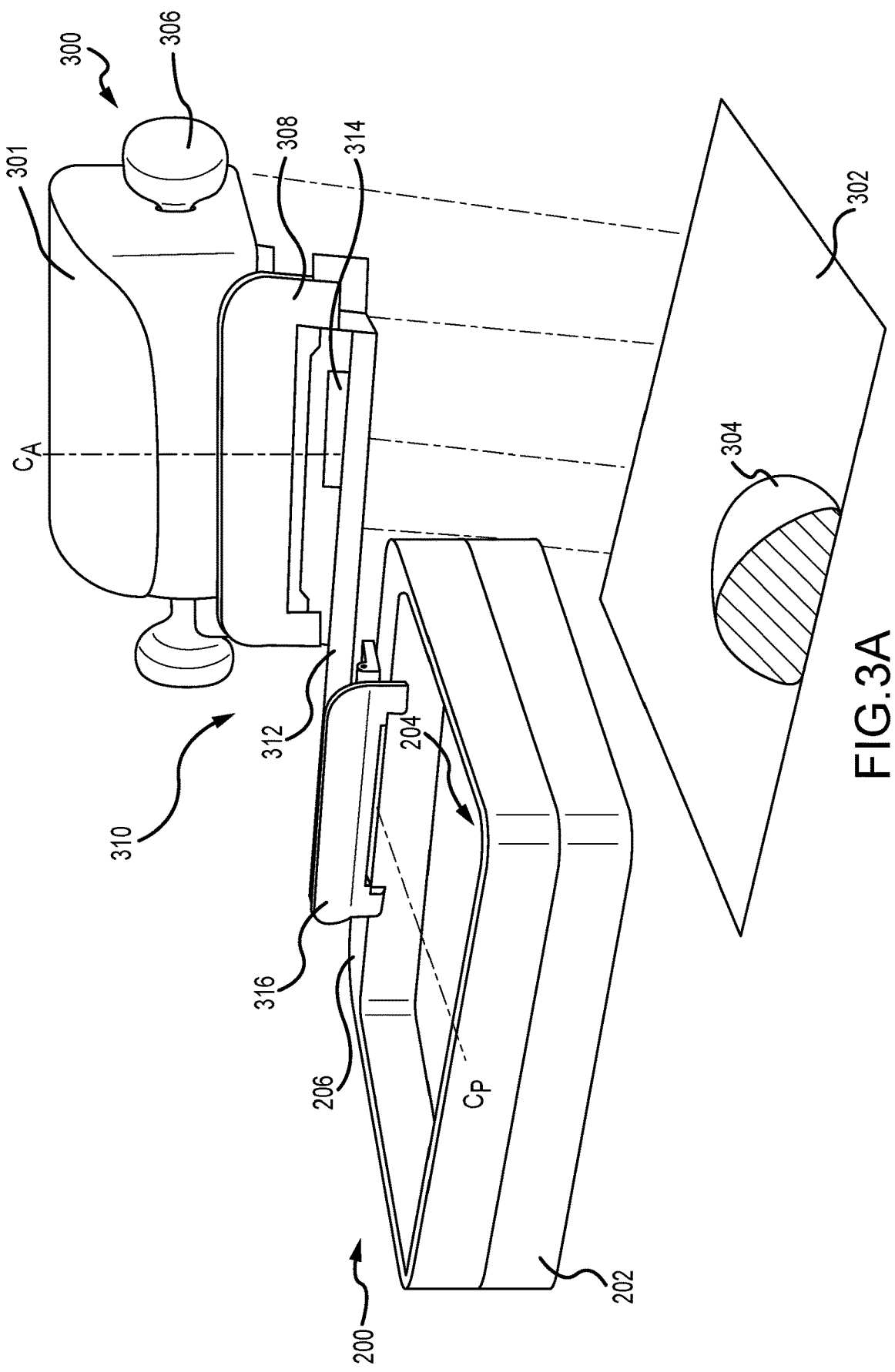
FIGS. 3A and 3B depict a breast compression paddle connected to a rail system, in a first position and a second position, respectively.
Figure 3B:
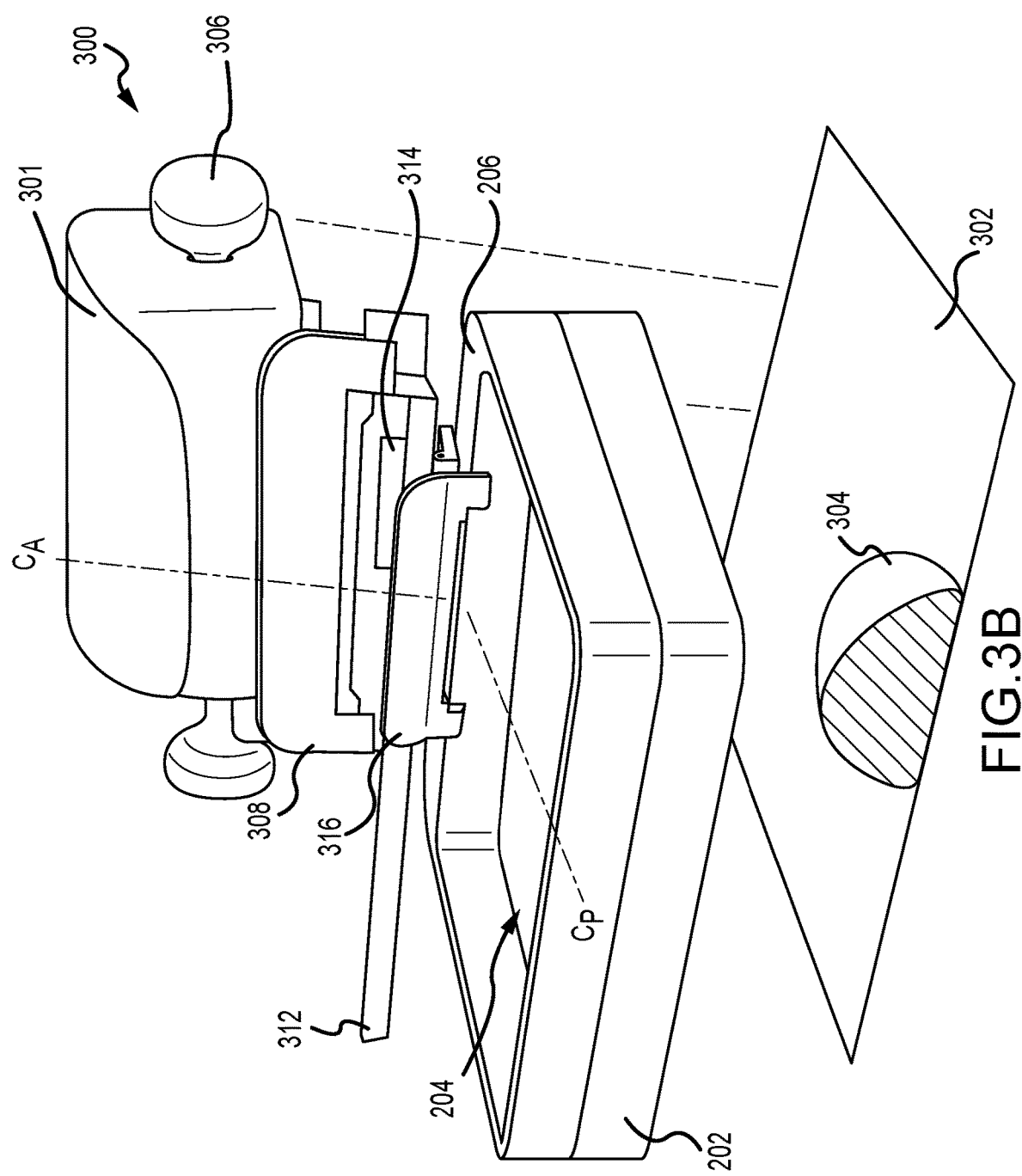

FIGS. 3A and 3B depict a breast imaging system 300 having a breast compression paddle 200 similar to that depicted in FIGS. 2A-2C, and connected to a rail system 310. FIGS. 3A and 3B are described concurrently. The breast compression paddle 200 includes a foam compressive element 202 that is secured to a bottom surface of the rigid substrate 204. A bracket portion 206 allows the breast compression paddle 200 to be secured to a compression arm 301 of the imaging system 300, such as depicted in FIGS. 1A and 1B, although not all elements thereof are depicted in FIGS. 3A and 3B. Other features of the breast compression paddle 200 are described above with regard to FIGS. 2A-2C and, as such, are not necessarily described further. The imaging system 300 includes a breast support platform 302 for supporting a breast (a testing phantom 304 is depicted). The compression arm 301 includes an actuator 306 that may be used to move the compression arm along an axis A substantially orthogonal to the support platform 301. The compression arm 301 includes a lever 308 that may be actuated to releasably connect a rail system 310 thereto. Typically, this is the lever 308 that connects a known rigid paddle to the compression arm 301. The rail system 310 includes, in this example, a single rail 312 that extends to one side of the compression arm 301. In other examples, the single rail 312 may extend to both sides of the compression arm 301, thus improving the versatility of the rail system 310. A rail system 310 that extends to both sides of the compression arm 301 may make access to the breast easier for a technician. In such an example, the compression paddle 200 may be slid in either direction, depending on which side of the imaging system the technician is standing, technician preference, or other factors.

Returning to the present example, a carriage 314 is movably engaged with the single rail 312. The carriage 314 may include rollers configured to roll along single rail 312. In another example, the carriage 314 may include one or more hooks or collars that surround the rail 312 and are configured to slide or glide thereon. Additional configurations are described herein. The rail 312 and/or the carriage 314 (or components thereof) may be manufactured from or coated with one or more low-friction materials to improve performance. The carriage 314 may include a lever 316 similar to the lever 308 described above, but that is configured to be releasably secured to the compression paddle 200, e.g., at the bracket portion 206 thereof.

FIG. 3A depicts the compression paddle 200 in a first position, where a centerline $C_A$ of the compression arm 301 is substantially aligned with a centerline $C_P$ of the compression paddle 200. Exact alignment is not required. Instead, here, the term "substantial alignment" refers to the position of the compression paddle 200 during compression and imaging procedures, that is, where the compression paddle 200 is typically centered on the compression arm 301, so as to distribute forces evenly on the breast 304. FIG. 3B depicts the compression paddle 200 in a second position. In this second position, the centerline $C_P$ of the compression paddle 200 is not substantially aligned with the centerline $C_A$ of the compression arm 301. In this second position, both sides of the rigid substrate 204 are disposed on a single side of the centerline $C_A$, while in the first position, the sides of the rigid substrate 204 are disposed on opposite sides thereof. In the second position, the compression paddle 200 is moved far to the side of the compression arm 301. In certain examples, a significant portion of the compression paddle 200 may extend beyond a side edge of the support platform 302. In examples, the centerline CP of the compression paddle 200 may be positioned beyond the side edge. In other examples, in the second position, a rightmost edge of the compression paddle 200 may be positioned beyond the leftmost side edge of the support platform 302. This range of motion of the compression paddle 200 greatly improves visibility of and access to the patient breast 304. Although the depicted configuration depicts the compression paddle 200 having a second position on a left side of the compression arm 301, in other examples, the second position of the compression paddle 200 be to the right of the compression arm 301. In other examples, the compression arm 200 may extend to both the left and the right sides of the compression arm 301.

In the depicted rail system 310, movement M of the compression paddle 200 is in a direction substantially parallel to the chest wall of the patient. With modification, however, the rail 312 may be include a slightly curved shape, which would allow the compression paddle 200 to move both to the side of the compression arm 301, and simultaneously generally towards or away from the patient.

Figure 4A:
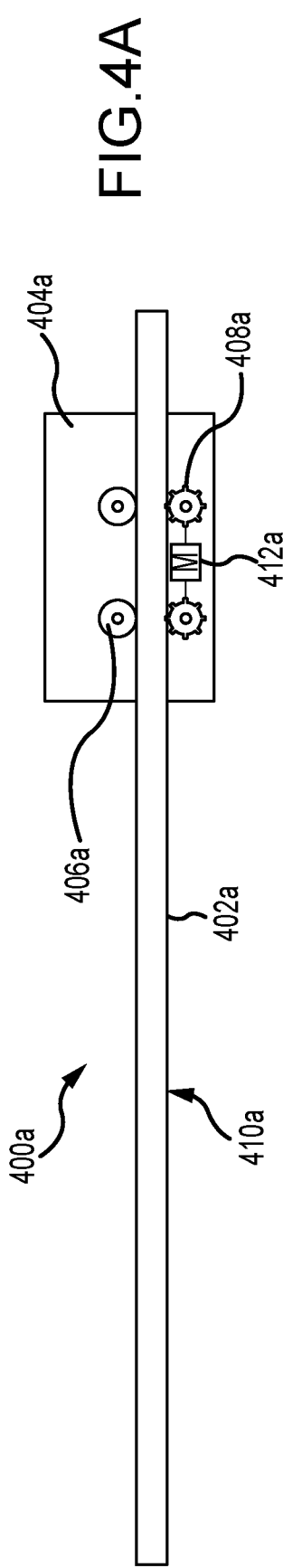
FIGS. 4A-4C depict various rail systems for use with an imaging system.
Figure 4B:
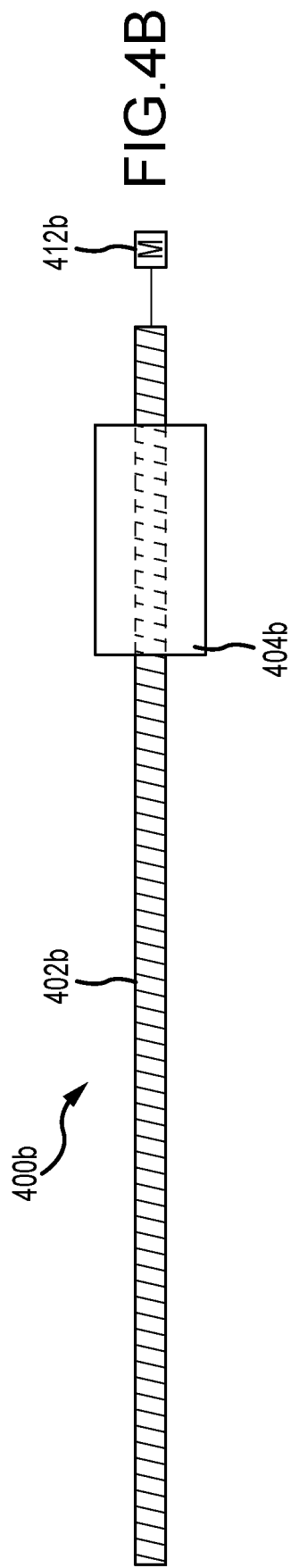
Figure 4C:
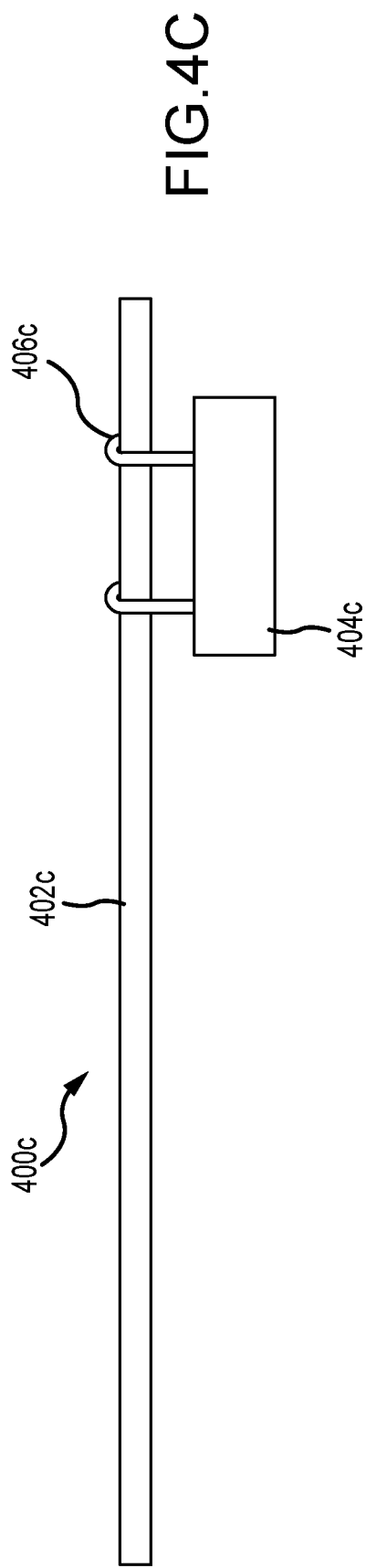

Movement M of the compression paddle 200 may be sliding movement. As used herein, the term "sliding" refers to the apparent movement of the compression paddle 200 relative to the compression arm 301, for example, as would be perceived by the patient. Sliding movement gives the impression of professional manufacturing of the imaging system, which may increase patient comfort with the compression and imaging procedures. Any type of rail system that produces this apparent sliding movement may be utilized. Various examples thereof are depicted in FIGS. 4A-4C. FIG. 4A, for example, depicts a rail system 400a including a rail 402a having a partially smooth outer surface and a carriage 404a movably disposed thereon. The carriage 404a includes a plurality of wheels or rollers 406a that engage the rail 402a on the upper side thereof and allows the carriage 404a to rollably move along the rail 402a. One or more gears 408a may be disposed on the underside of the rail 402a, which may define a rack 410a for engagement by the gears 408a. The gears 408a may be driven by a motor 412a so as to actuate the carriage 404a to move along the rail 402a. In other examples, the rail system need not be motorized and instead may include rollers above and/or below the rail. In that configuration, the carriage 404a (and compression paddle attached thereto) may be manually actuated from the first position to the second position. FIG. 4B depicts another example, where the rail system 400b includes a rail 402b in the form of a lead screw. A carriage 404b in the form of or including a nut may be engaged with the lead screw 402b, so as to be moved therealong. A motor 412b may rotate the lead screw 402b so as to actuate the carriage 404b. In another example, depicted in FIG. 4C, the rail system 400c includes a smooth rail 402c. A plurality of hangers or collars 406c at least partially engage and/or surround the rail 402c and connect the rail 402c to a carriage 404c. The hangers 406c and/or rail 402c may be coated with a low friction coating or may be made from a low-friction material. As noted above, a compression paddle may be connected to any of the carriages depicted in FIGS. 4A-4C with a bracket, as known in the art. The rail systems 400A-400C may be modified as needed and utilized with another example of a rail system, described in the context of FIGS. 5A and 5B. The modifications required will be apparent to a person of skill in the art.

Figure 5A:
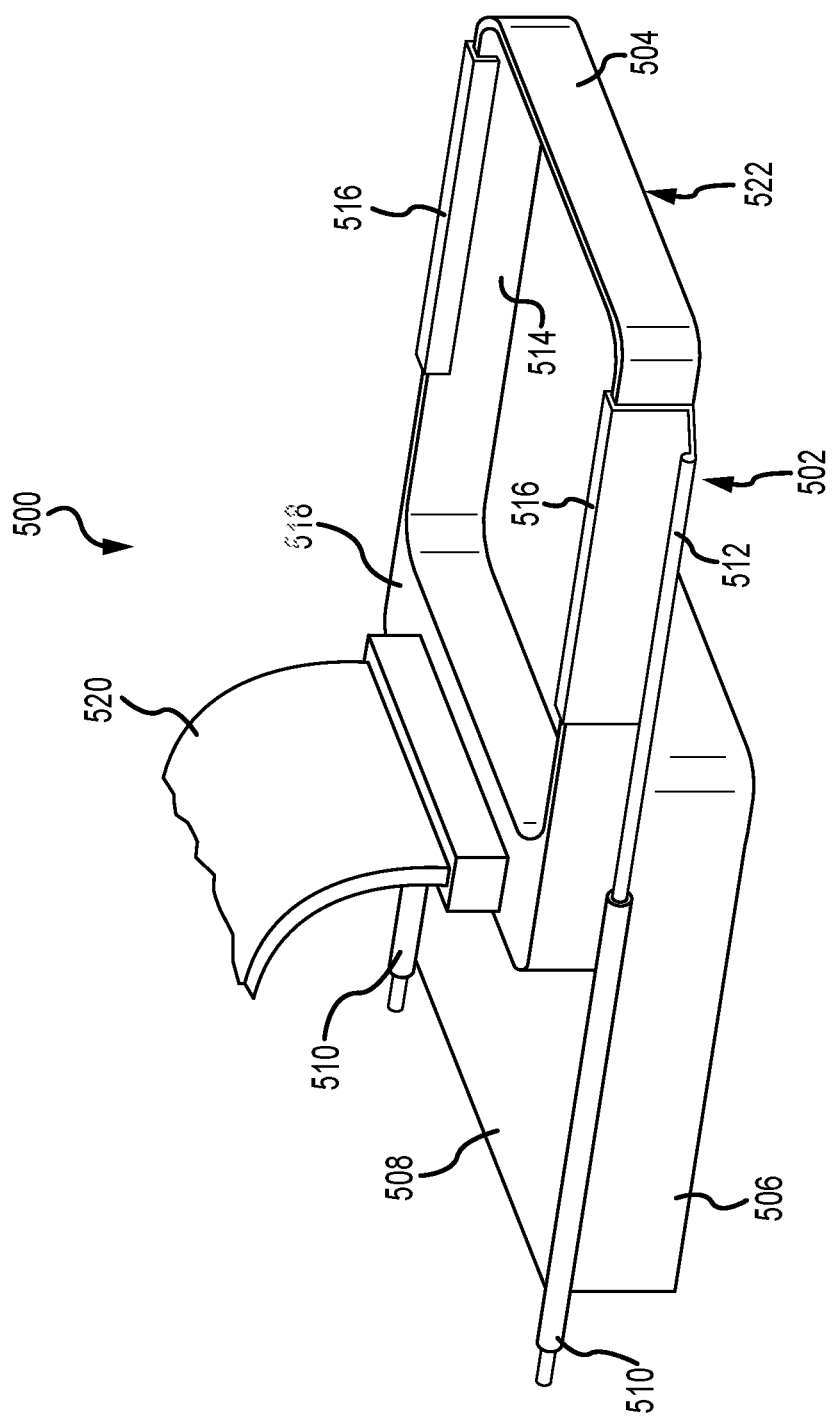
FIGS. 5A and 5B depict a breast compression paddle connected to a rail system and foam compressive element, in a first position and a second position, respectively.
Figure 5B:
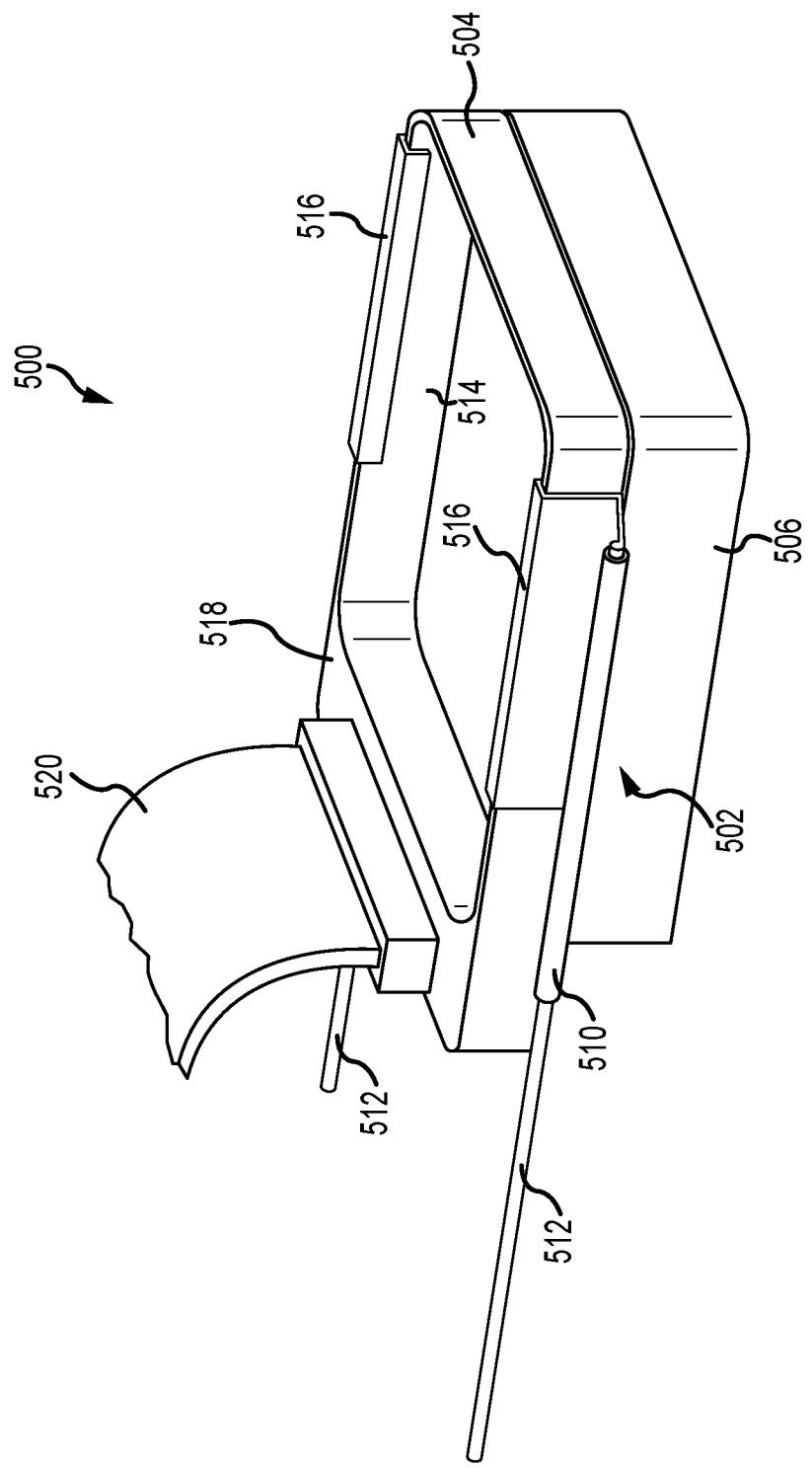

FIGS. 5A and 5B depict a breast compression paddle 500 having a rail system 502 incorporated therein. Unlike the example of FIGS. 3A and 3B, where a compression paddle is removably secured to a slidable carriage which is in turn removably secured to a compression arm, the example of FIGS. 5A and 5B utilizes a compression paddle 500 made from a rigid substrate 504 and a foam compressive element 506 movable secured thereto via the rail system 502. More specifically, the foam compressive element 506 is secured to a bridge 508, which may be rigid, semi-rigid, or flexible. In examples, the bridge 508 is a radiopaque screen that spans two collars 510, one disposed proximate each side of the foam compressive element 506. The collars 510 are slidably engaged with two rails 512, one disposed proximate each sidewall 514 of the rigid substrate 504. The rails 512 may be integrally formed with a larger attachment portion 516 that is configured to be attached (e.g., hung, although mechanical fasteners may also be used) to a sidewall 514 of the rigid substrate 504. Although a low-friction collar 510 slidably engaged with a rail 512 is depicted, other configurations may be utilized, such as those depicted above in FIGS. 4A-4C. As such, consistent with that disclosure, the rail system 502 depicted in FIGS. 5A-5B may be motorized.

The compression paddle 500 includes a bracket 518 that may be removably secured to a compression arm 520 of an imaging system, as known in the art. In examples, the rigid substrate 504 may be any known in the art having a flat, concave, or other bottom compressive surface 522. The rail system 502 may be secured thereto and the foam compressive element 506 may be movably secured to the rail system 502. Thus, the foam compressive element 506 is movably secured relative to the rigid substrate 504 of the compression paddle 500. In this case, the slidable movement of the foam compressive element 506 is substantially orthogonal to the chest wall of the patient. That is, in the first position depicted in FIG. 5A, the foam compressive element 506 is disposed substantially below or behind (relative to a patient) the bracket 518 and compression arm 520. In the second position depicted in FIG. 5B the foam compressive element 506 is disposed substantially below the rigid substrate 504 (and in front of the bracket 518, relative to the patient).

Figure 6:
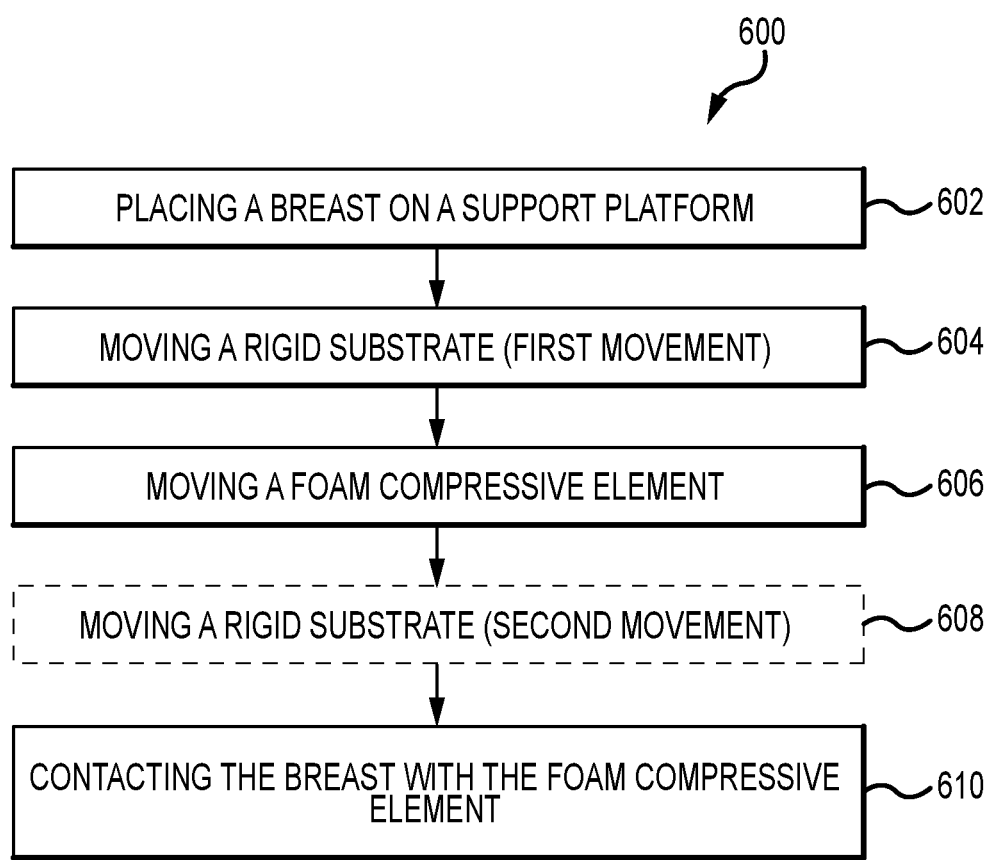
FIG. 6 depicts a method of positioning a breast for x-ray imaging.

FIG. 6 depicts a method 600 of positioning a breast for x-ray imaging. The method begins with placing a breast on a support platform, operation 602, for example, of an x-ray imaging system such as a tomosynthesis, mammography, or combination system, as described elsewhere herein. Once the breast is so supported, the method 600 continues with operation 604, moving a rigid substrate in a direction substantially orthogonal to the support platform on which the breast rests. This movement, in one example, is consistent with lowering a compression paddle towards the breast and support platform, while the technician holds the breast in place. Due to the position of the compression paddle (e.g., not directly above the breast) or the material of the rigid substrate (e.g., translucent or transparent), the breast remains largely within view of the technician, allowing the technical to positon and reposition the breast as needed. The method 600 continues with moving a foam compressive element, operation 606, in a direction substantially parallel to the support platform. In examples, consistent with those provided herein, this may include also moving the rigid substrate in a direction substantially parallel to the support platform or, in other examples, the rigid substrate need not be moved in a direction substantially parallel to the support platform. Further, this movement of the foam compressive element may be substantially parallel to or orthogonal to the chest wall of the patient, depending on the system used. In other examples, movement in two axes (relative to the chest wall) is also contemplated.

The method 600 continues with operation 608, moving the rigid substrate. In examples, this operation may include moving the rigid substrate in a direction substantially parallel to the support platform. This operation contemplates movement between a second position, where the compression paddle is not substantially centered on the support platform, to the first position, where it is. These positions are described elsewhere herein. For example, if used with the assembly depicted in FIGS. 3A and 3B, this movement may be performed at the same time that the foam compressive element is moved in operation 606. In another example, operation 608 may be performed after the foam compressive element (e.g., the foam compressive element 506 of FIGS. 5A and 5B) has been moved to a position below the rigid substrate. In that example, then, operation 608 contemplates moving the rigid substrate and the foam compressive element together toward the breast. Regardless, as the rigid substrate and foam compressive element are further lowered towards the breast, contact is made between the breast and the foam compressive element, e.g., operation 610. Once contact is made, compression of the breast may be increased by increasing pressure applied by the paddle to the breast tissue. Once the desired compressive force is reached, imaging may be performed. Of course, certain of these operations may be reversed in whole or in part to free the breast from compression. Further, a number of these operations (e.g., lowering the rigid substrate and the foam compressive element, moving the rigid substrate and/or the foam compressive element in a direction substantially parallel to the support platform) may be performed by one or more motors, which may be controlled by a controller on the imaging system, or may be performed manually.

Figure 7:
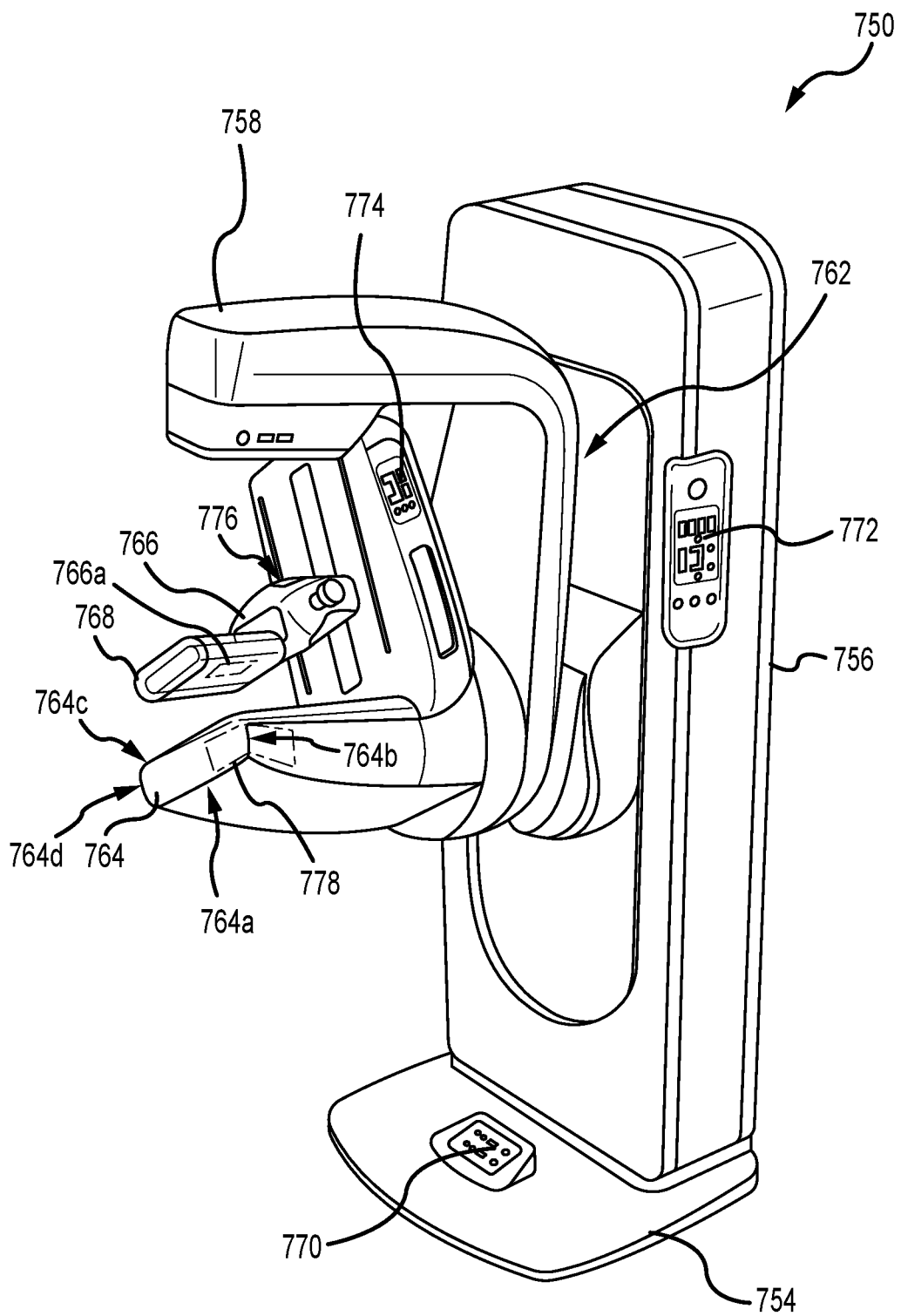
FIG. 7 depicts the x-ray imaging system in a breast positioning state for left mediolateral oblique (LMLO) imaging orientation.

FIG. 7 depicts an exemplary x-ray imaging system 750 in a breast positioning state for left mediolateral oblique MLO (LMLO) imaging orientation. A tube head 758 of the system 750 is set in an orientation so as to be generally parallel to a gantry 756 of the system 750, or otherwise not normal to the flat portion of a support arm 760 against which the breast is placed. In this position, the technologist may more easily position the breast without having to duck or crouch below the tube head 758.

The x-ray imaging system 750 includes a floor mount or base 754 for supporting the x-ray imaging system 750 on a floor. The gantry 756 extends upwards from the floor mount 752 and rotatably supports both the tube head 758 and a support arm 760. The tube head 758 and support arm 760 are configured to rotate discretely from each other and may also be raised and lowered along a face 762 of the gantry so as to accommodate patients of different heights. An x-ray source, described elsewhere herein and not shown here, is disposed within the tube head 758. The support arm 760 includes a support platform 764 that includes therein an x-ray receptor and other components (not shown). A compression arm 766 extends from the support arm 760 and is configured to raise and lower linearly (relative to the support arm 760) a compression paddle 768 for compression of a patient breast during imaging procedures. In the depicted example, the compression paddle 768 is a rigid compression paddle 768. Together, the tube head 758 and support arm 760 may be referred to as a C-arm. A number of interfaces and display screens are disposed on the x-ray imaging system 750. These include a foot display screen 770, a gantry interface 772, a support arm interface 774, and a compression arm interface 776. In general the various interfaces 772, 774, and 776 may include one or more tactile buttons, knobs, switches, as well as one or more display screens, including capacitive touch screens with graphic user interfaces (GUIs) so as to enable user interaction with and control of the x-ray imaging system 750.

Although many of the edges of the imaging system 750 that may contact a patient are rounded, discomfort can still occur since those edges are manufactured of rigid plastics, even though those edges are considered "non-compressive" in that they are not intended to apply a compressive force to the breast. More specifically, the support platform 764 primarily contacts the patient at edges 764a and 764c when the patient is being imaged in the CC imaging orientation, primarily at the chest wall. Side edges 764b and 764c may also contact the patient in the MLO imaging orientations. Another aspect of the technology contemplates improving patient comfort by applying discrete foam compressive elements at one or more of these edges, even though these edges not considered compressive surfaces in the same context that the compression paddle 768 or support platform 764 are so considered. One such foam compressive element 778 is depicted with dashed lines covering edge 764b.

Figure 7A:
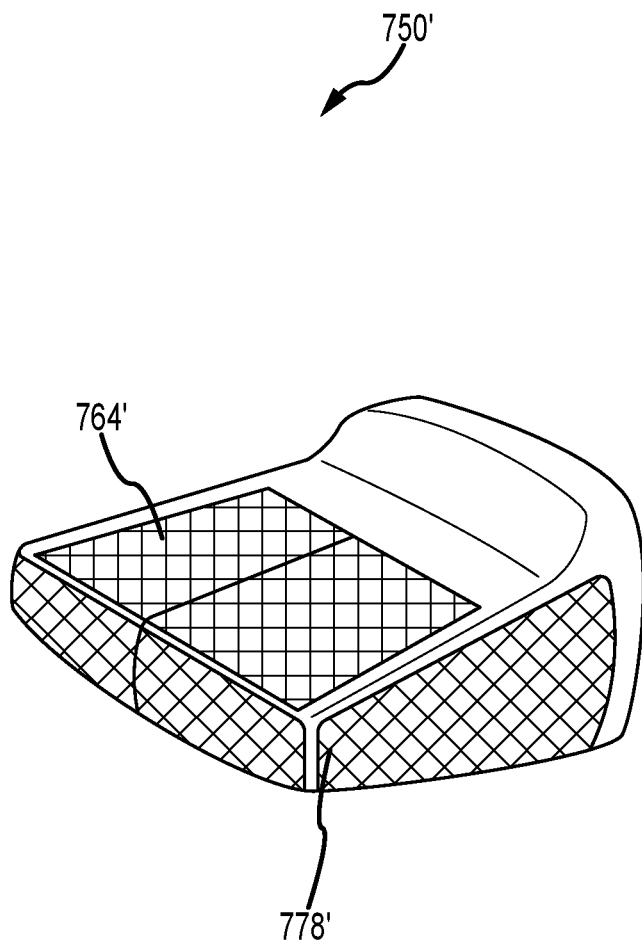
FIG. 7A depicts a partial perspective view of another example of an x-ray imaging system.

FIG. 7A depicts a partial perspective view of another example of an x-ray imaging system 750', more specifically, the support platform 764'. A foam compressive element 778' extends along the entire front face of the support platform 764', as well as a side face thereof. This configuration helps cushion the patient's axilla skin, especially during MLO imaging procedures. In examples, the foam compressive element 778' may be covered with a water- or moisture-proof coating that may prevent absorption of bodily fluids (e.g., sweat, blood, etc.) into the foam. The coating may be cleanable so as to enable use between subsequent patients, or the entire foam compressive element 778' may be removeable and disposable to maintain desired sanitary conditions between patients.

Returning to FIG. 7, certain patients, such as those who have undergone a lumpectomy, cyst removal, lift, etc. may experience particular discomfort at the site of said procedure. Thus, the technologies described herein also contemplate applying a discrete foam compressive element 768a to a particular location of the compression paddle 768 (or support platform 764) where the site is expected to contact the rigid compressive surface. These configurations (e.g., covering discrete portions of the rigid compressive surfaces, as opposed to substantially the entire portion of the rigid compressive surface, as is the case with the larger foam compressive elements of FIGS. 2A-2C. The discrete foam compressive element 768a may cover about 10%, about 20%, about 30%, or about 50% of the compressive surface of the compression paddle 768 or support platform 764, where the compressive surface is defined as the portion of said component that actually contacts the breast at full compression for an imaging procedure.

Figure 8A:
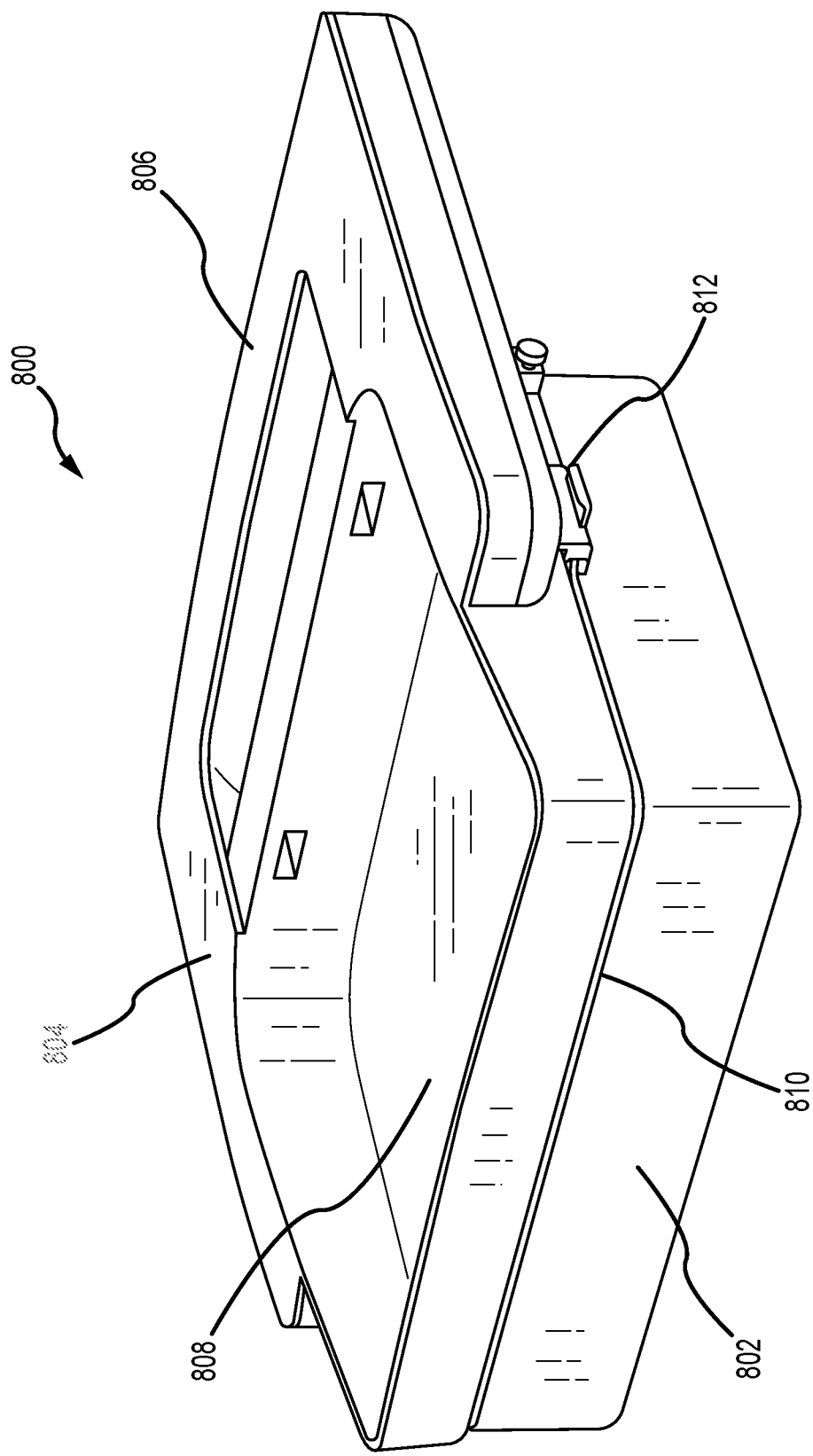
FIGS. 8A and 8B depict a perspective view and an exploded perspective view, respectively, of another example of a breast compression paddle having a foam compression element.
Figure 8B:
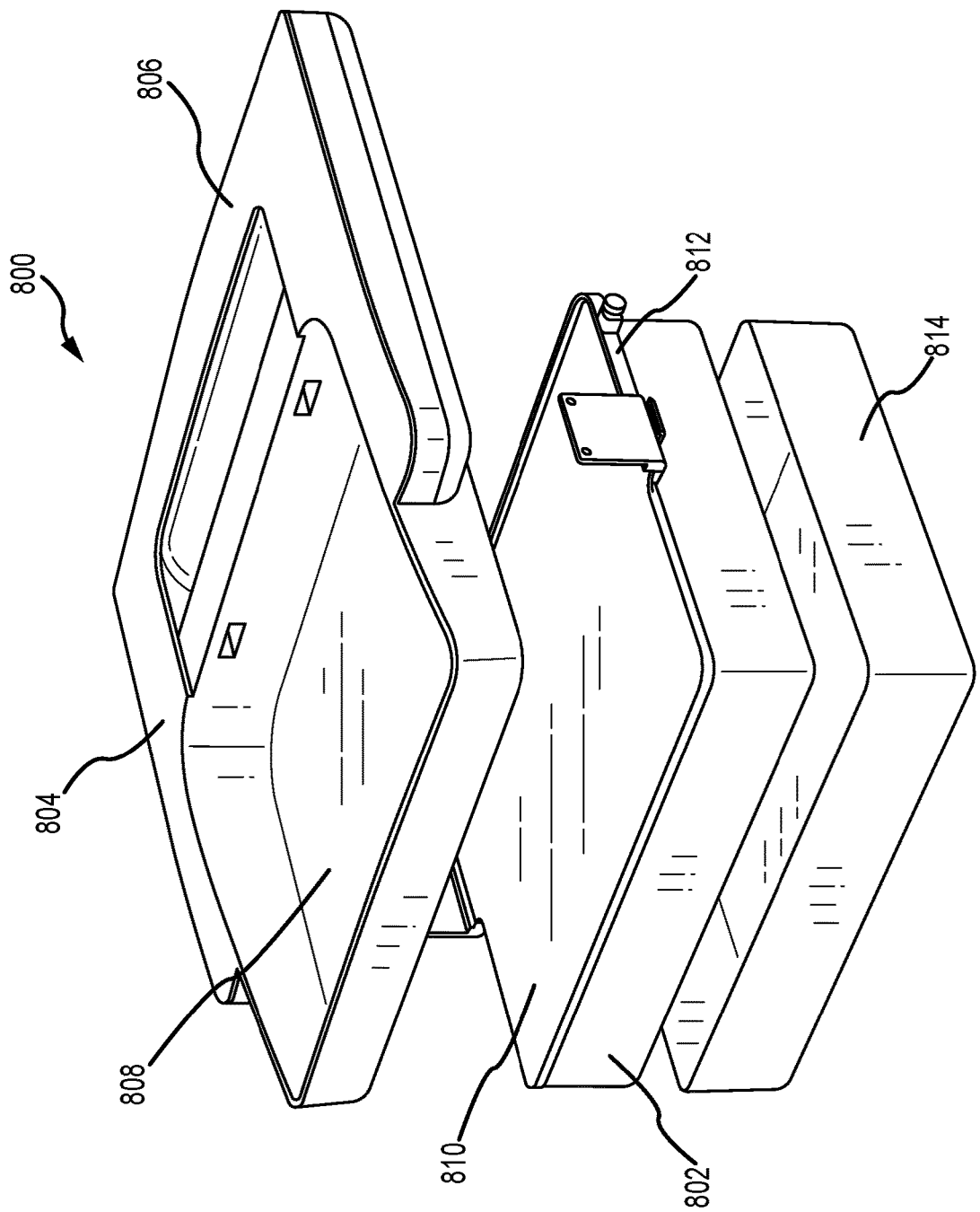

FIGS. 8A and 8B depict a perspective view and an exploded perspective view, respectively, of another example of a breast compression paddle 800 having a foam compressive element 802. FIGS. 8A and 8B are described concurrently. The paddle 800 includes a bracket 804, which may be formed of one or more rigid (as compared to the foam compressive element 802) parts. For example, the bracket 804 may include a connection portion 806, where the bracket 804 may be connected to an imaging system, as well as a compressive region 808, depicted in FIG. 8A as the flat surface above the foam compressive element 802. This compressive region 808 transfers the force applied by the imaging system to the foam compressive element 802 (and ultimately to the breast disposed below). The foam compressive element 802 may be secured to a rigid substrate 810, which may be received in a substrate receptacle 812 that is movably secured to the bracket 804, e.g., at the connection portion 806, as described further herein. A disposable cover 814 is also depicted, but need not be utilized. Disposable covers 814 may allow the otherwise absorbent foam compressive elements 802 to be reused with different patients, even though the foam material is absorbent.

Figure 8D:
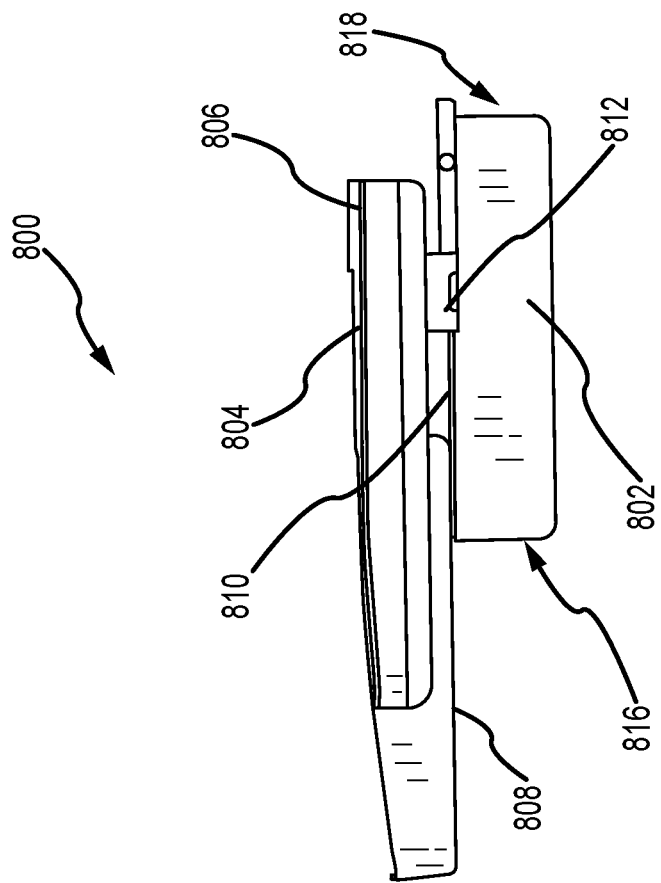
FIGS. 8C and 8D are side views of the breast compression paddle of FIGS. 8A and 8B having the foam compression element, in a first position and a second position, respectively.
Figure 8C:
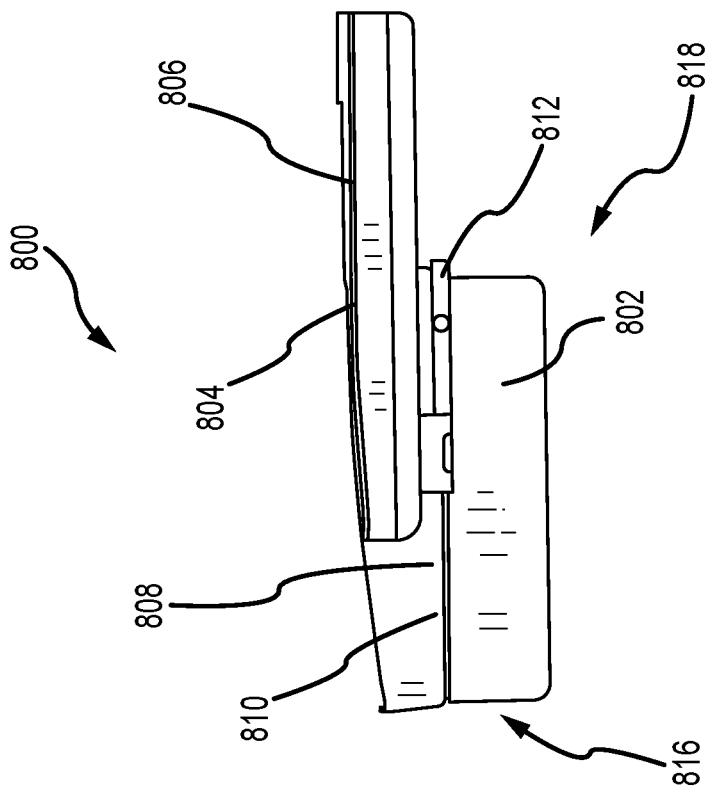

FIGS. 8C and 8D are side views of the breast compression paddle 800 of FIGS. 8A and 8B having the foam compressive element 802, in a first position and a second position, respectively. The elements of the paddle are described above in the context of FIGS. 8A and 8B and are not necessarily described further. Both the foam compressive element 802 and the rigid substrate 810 may be described has having edges or edge surfaces. For example, both components have a first edge or edge surface 816 (depicted on the foam compressive element 802 only for clarity) and a second edge or edge surface 818 (again depicted on the foam compressive element 802 only for clarity) disposed opposite the first. As can be seen in FIG. 8C, when the foam compressive element 802 and the rigid substrate 810 are disposed below the compressive region 808 of the bracket 804, compressive force is transferred from the imaging system through the foam compressive element 802 and to the breast. In this first position, in the depicted example, both of the first edge 816 (and edge surface) and the second edge 818 (and edge surface) are disposed below the compressive region 808 to help ensure an even force distribution. In FIG. 8D, the foam compressive element 802 and the rigid substrate 810 have been moved to the second position. This movement is enabled by movement of the substrate receptacle 812 relative to the bracket 804, as described further herein. When in the second position, only the first edge 816 (and edge surface) is disposed below the compressive region 808. In the second position, compression of the breast is typically not performed, but by disposing the foam compressive element 802 in the location depicted, access to the breast by the technician for positioning may be improved. Further, but disposing the foam compressive element 802 in the second position, a visible light that is substantially coextensive with the emitted x-ray radiation may be more easily aligned with the breast, to help ensure proper x-ray imaging.

Figure 8E:
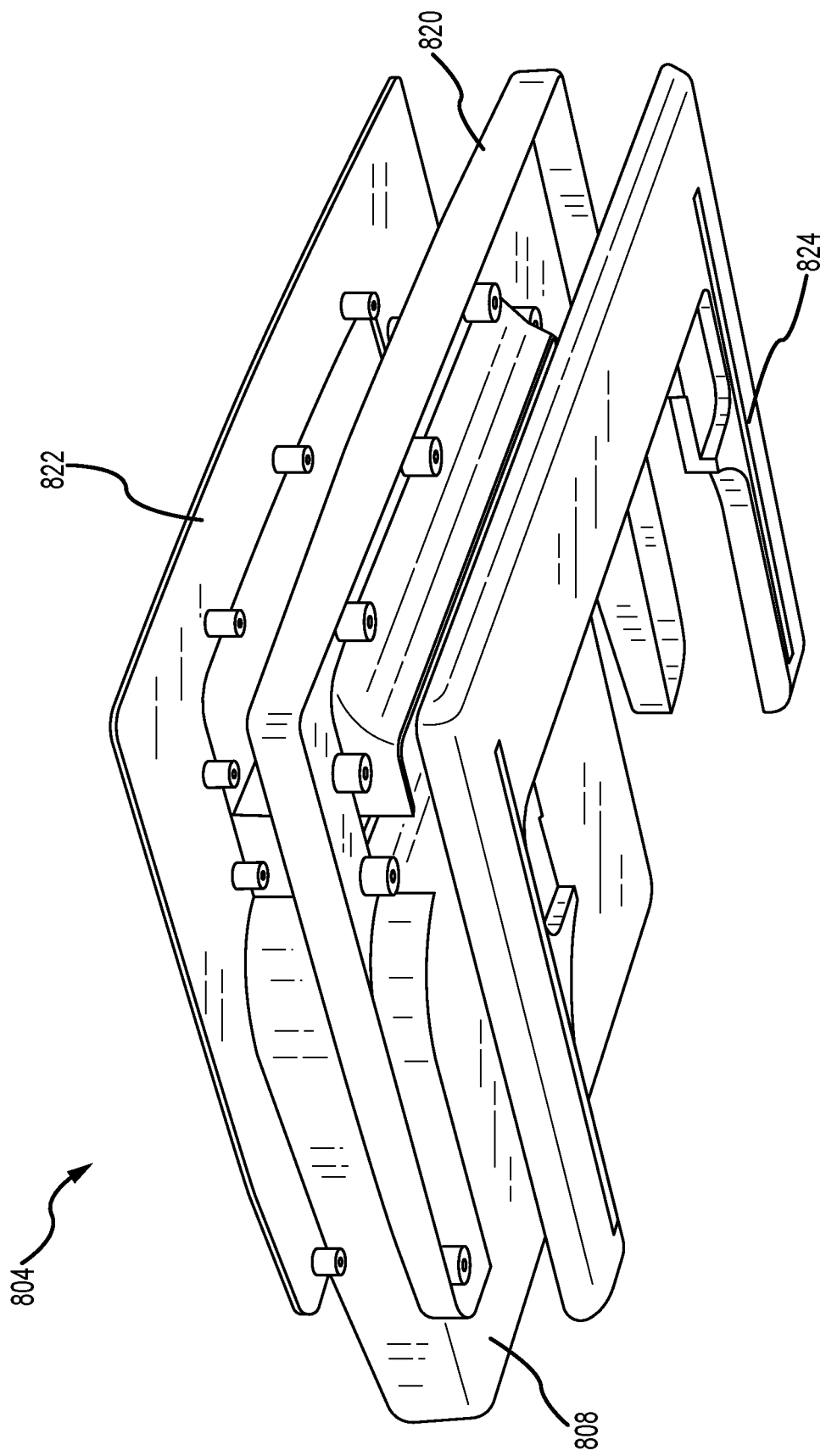
FIG. 8E depicts an exploded perspective view of a bracket of the breast compression paddle of FIGS. 8A-8D.

FIG. 8E depicts an exploded perspective view of a bracket 804 of the breast compression paddle of FIGS. 8A-8D. In the depicted example, three main parts or components are utilized. These include a chassis 820, a top cover 822, and a bottom cover 824. While each part may be formed of robust molded plastic (e.g., as known in paddle manufacturing) it may be advantageous to manufacture the chassis 820 of cast and/or machined metal, since the drive system for moving the foam compressive element is disposed therein. The top cover may be manufactured from molded radiolucent plastic, primarily due to its incorporation of the compressive region 808, as well as the connection portion 806. In other examples, the chassis 820 may form all or a part of the connection portion, which may add additional structural integrity to the bracket 804. The bottom cover 824, made of molded plastic, may be incorporated to improve aesthetics.

Figure 8F:
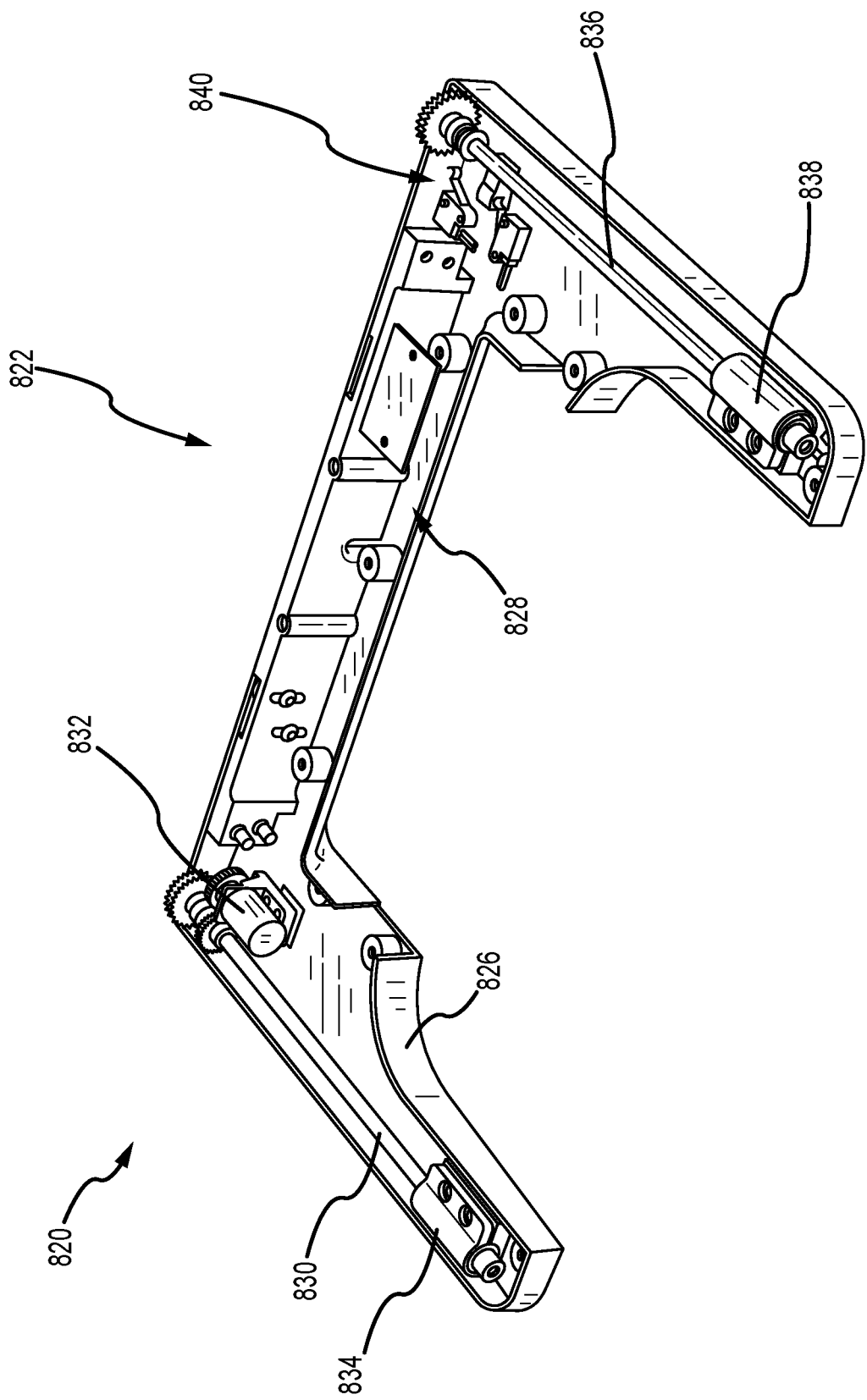
FIG. 8F depicts an interior view of a chassis of a breast compression paddle.

FIG. 8F depicts an interior view of the chassis 820, which may include a body 826 made from materials as described above. The body at least partially defines a hollow interior volume 828 in which may be disposed components of a drive system. The drive system may include one or more lead screws 830, which may be driven by a motor 832. Rotation of the lead screw 830 by the motor 832 advances a nut 834 axially therealong. The nut 834 is connected to the substrate receptacle as described elsewhere herein. To balance forces, the drive system may also include a rail 836 disposed opposite the lead screw 830, with a bearing mount 838 movably disposed therealong. The bearing mount 838 is connected to an opposite side of the substrate receptacle, in a configuration that may be similar to the connection between the substrate receptacle and the nut 834. One or more encoders 840 or other position sensors may be disposed in various locations to detect movement (e.g., rotational, linear, relative positional) of the various components. In yet another example, both elements 830 and 836 may be lead screws, with elements 834 and 838 being nuts. In such a configuration, a belt (not depicted) may connect the two lead screws and the single motor 832 may drive the rotation of both lead screws 830, 836. Drive systems utilizing multiple motors (e.g., two unidirectional motors or two motors rotating a single one of two lead screws) may also be utilized. Other drive systems may also be utilized. For example, chain, belt, or cable drive systems are contemplated. A rack and gear drive system may also be utilized. In another example, one or both of the lead screw 830 and the rail 836 may be replaced with a maglev system.

Figure 9A:
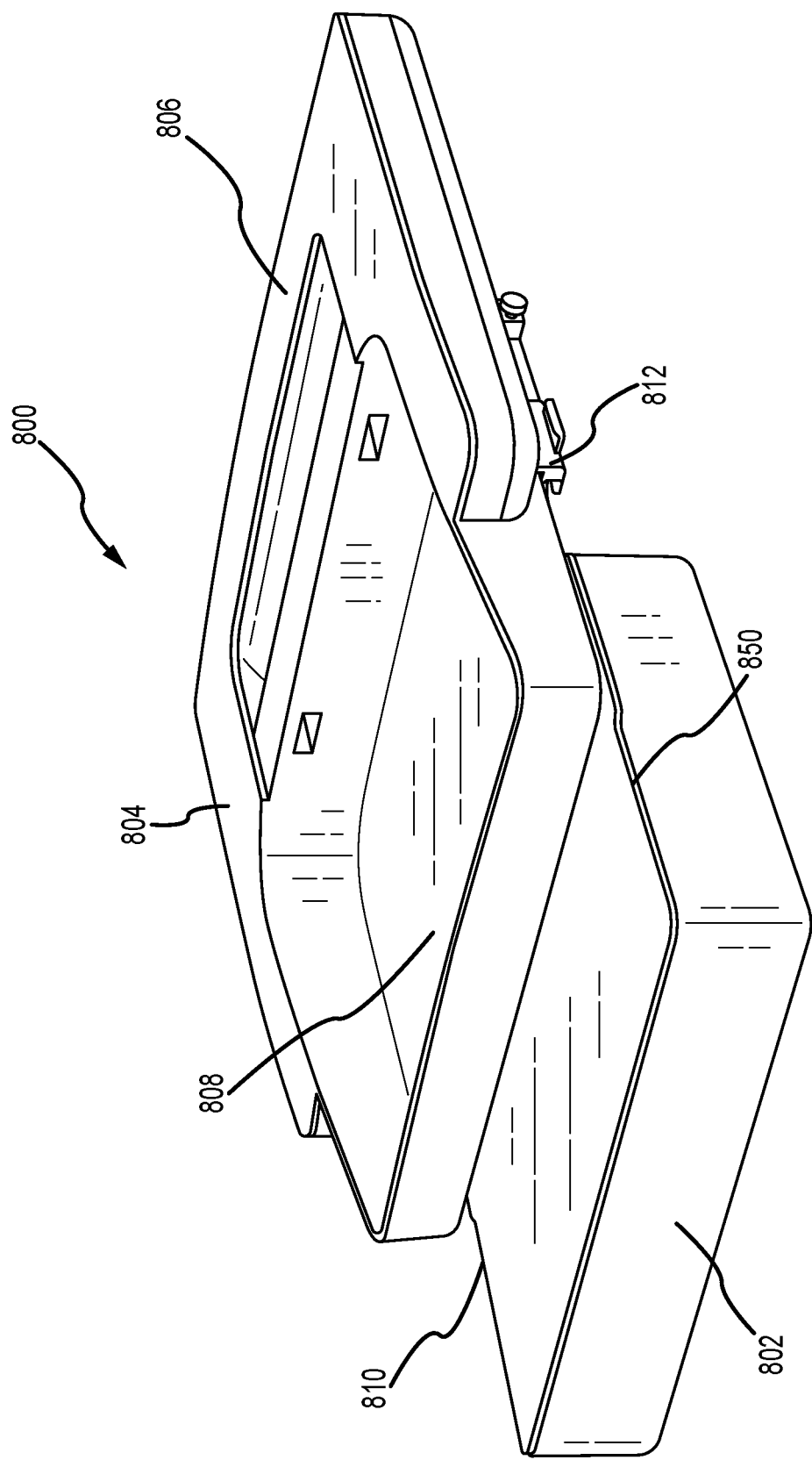
Figure 9B:
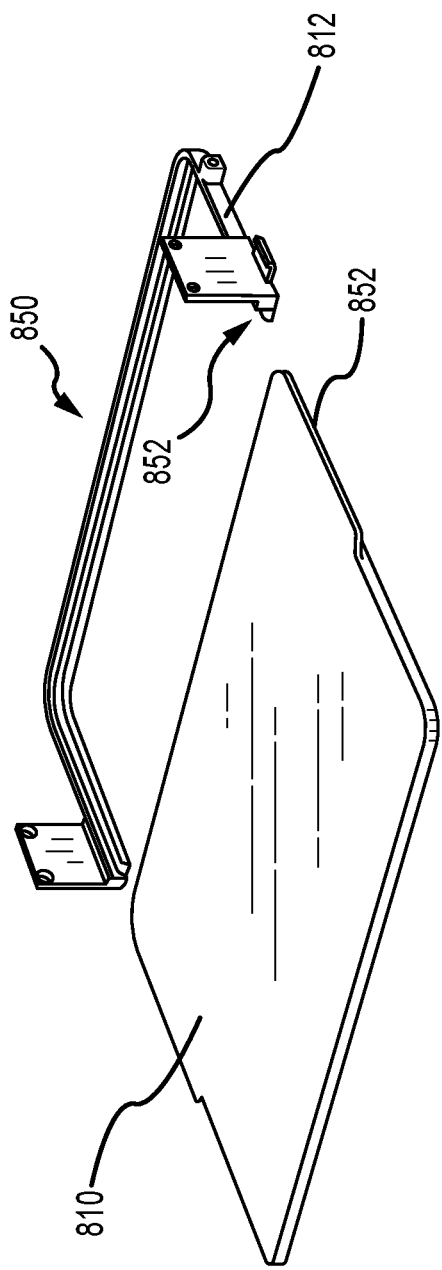
Figure 9C:
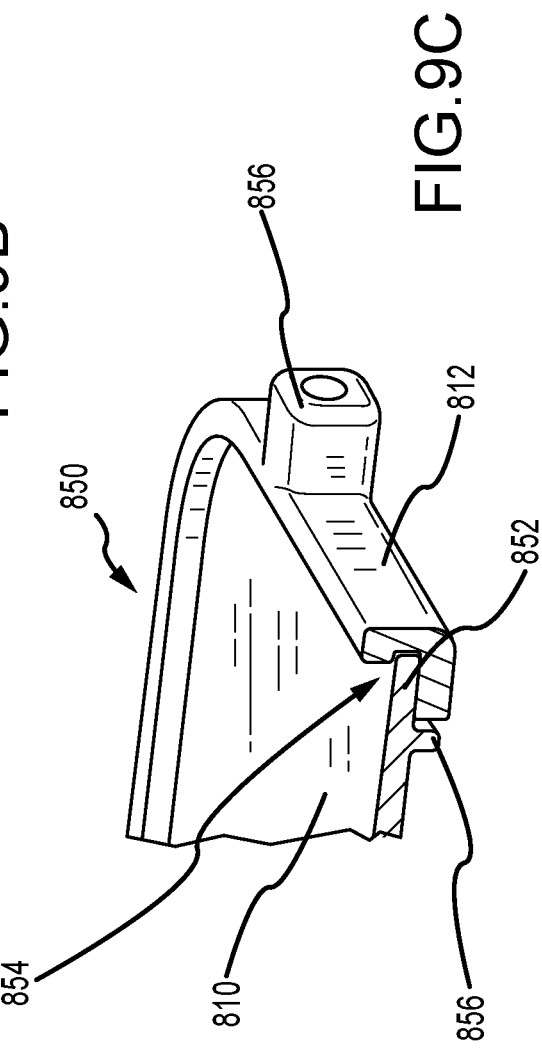

FIGS. 9A-9F depicts various views of components of a connection system 850 for connecting a foam compressive element 802 to a compression paddle 800. FIGS. 9A-9F are described concurrently, but not all components are necessarily depicted in every figure, nor described again, as these features are depicted above with regard to FIGS. 8A-8F. FIG. 9A is a perspective view of a compression paddle 800 during installation of a foam compressive element 802, via the connection system 850. The foam compressive element 802 is mounted to the rigid substrate 810, which includes a plurality of edges 852, which project outward beyond the sides of the foam compressive element 802. In examples, the plurality of edges 852 may project from a portion of the sides of the rigid substrate 810, as depicted in this example. Further, the plurality of edges 852 also project from a rear of the rigid substrate 810, allowing for greater engagement. The substrate receptacle 812 defines a groove 854 for receiving the plurality of edges 852. A flange 856 (most readily visible in FIG. 9C) projects from a lower surface of the rigid substrate 810 and may be used to help guide the rigid substrate 810 into the groove 854 of the substrate receptacle 812. The substrate receptacle 812 may include a housing 858 projecting from a side thereof. The housing 858 is configured to receive a movable pin 860 that includes a head 862 and a tip 864. When the pin 860 is in the retracted position depicted in FIGS. 9D and 9E, the rigid substrate 810 may be slid into and out of the substrate receptacle 812. When the rigid substrate 810 is fully inserted into the substrate receptacle 810, the pin 860 may be advanced to the extended position, such that the tip 864 may project into a recess 866 defined by an edge 852 of the rigid substrate 810. In examples, the tip 864 may be biased into the extended position depicted in FIG. 9F, e.g., with a spring disposed in the housing 858. In another example, the tip 864 may include a tapered leading edge so as to ease insertion of the rigid substrate 810 into the substrate receptacle 812. The pin 860 may also be configured to remain in the extended position of FIG. 9F unless manipulated in a particular sequence (e.g., rotated before retraction).

Figure 9G:
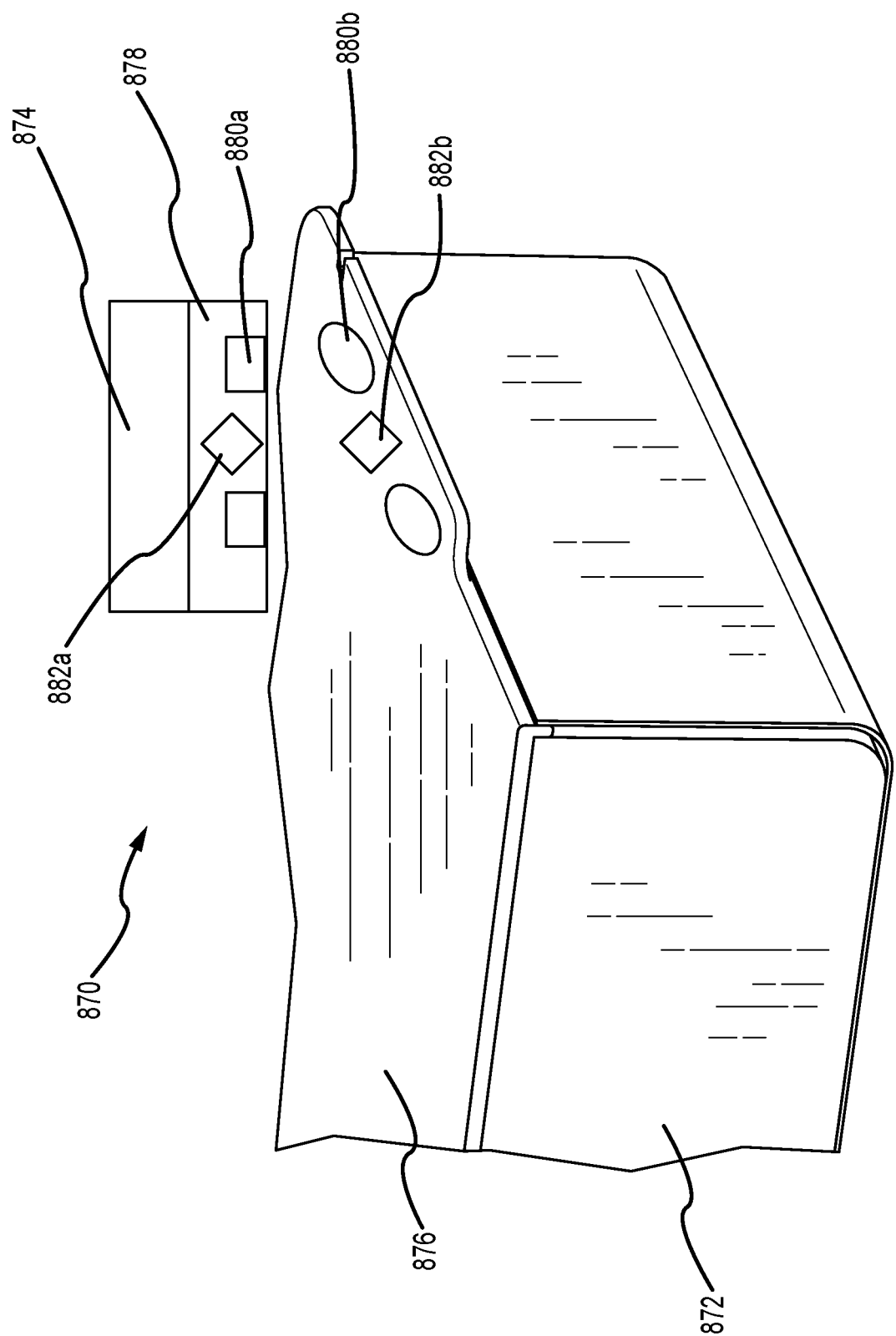
FIG. 9G depicts another example of a connection system for connecting a foam compressive element to a compression paddle.

FIG. 9G depicts another example of a connection system 870 for connecting a foam compressive element 872 to a compression paddle 874. As depicted elsewhere herein, the foam compressive element 872 is secured to a rigid substrate 876. The compression paddle 874 includes a mount 878 moveably secured to a drive system within the compression paddle 874, e.g., as depicted in FIG. 8F. The mount 878 may include a number of features that enable connection to the rigid substrate 866. For example, one or more magnets 880a may be configured to engage with corresponding magnets 880b on the rigid substrate 876. The magnets 880a, 880b may be neodymium magnets, electromagnets or other magnets that may robustly secure the rigid substrate 866 to the mount 878, especially during the movements and compressions described herein. Mating alignment features 882a, 882b on both the mount 878 and rigid substrate 876, which may be in the form of mating raised and recessed structures, shaped magnets, etc. may also help in aligning the magnets and further securing the rigid substrate 876.

Figure 10B:
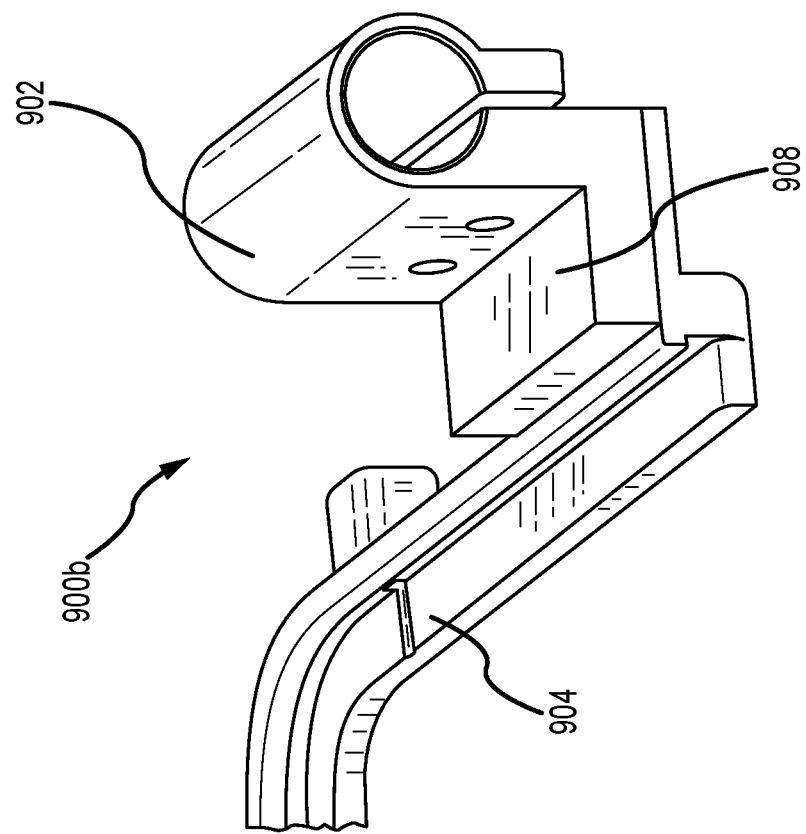
FIGS. 10A and 10B depict examples of an interface between a mount and a substrate receptacle.
Figure 10A:
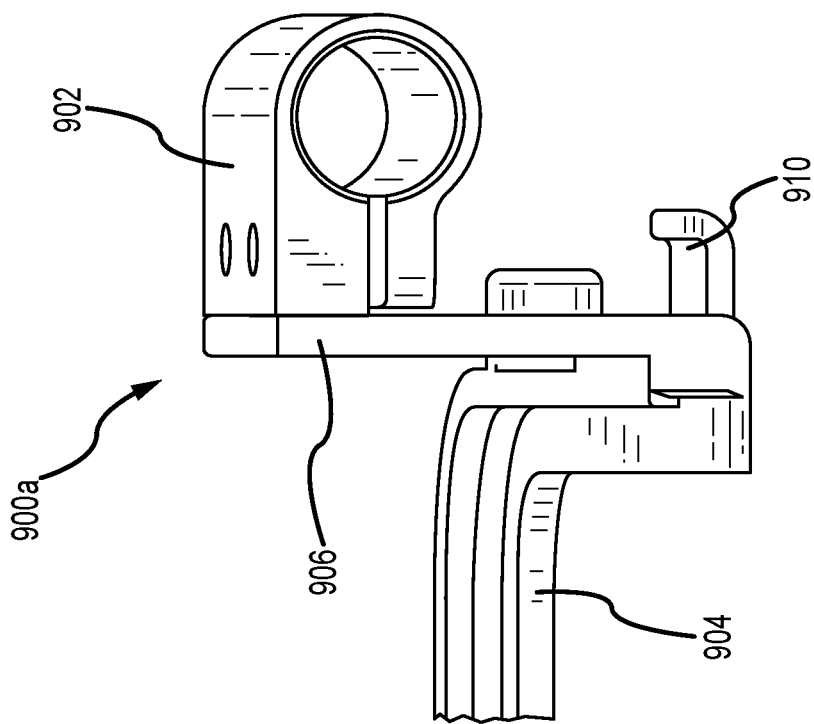

FIGS. 10A and 10B depict examples of an interface 900 between a mount 902 and a substrate receptacle 904. In the interface 900a of FIG. 10A, the substrate receptacle 904 may include a vertical projection 906 that may extend upwards and into the chassis (not shown) where it is connected to the mount 902. In the interface 900b, the mount 902 may include an extension 908 that may extend downward and out of the chassis (not shown) where it is connected to the substrate receptacle 904. These interface 900a, 900b configurations are two of several examples of interfaces that may be utilized. In general, elongate extensions 908 may be desirable to provide clearance between the substrate receptacle 904 and the bottom cover of the bracket (not shown). This increased clearance reduce interference during movement of the foam compressive element, increase access to other components of the receptacle, as described elsewhere herein, or otherwise allow for improved access to the patient breast or other system components. The substrate receptacle 904 may also include a hook 910 or other feature for attaching a disposable cover (e.g., used to cover the foam compressive element) to the receptacle 904 for easy removal and replacement thereof between different patients.

FIGS. 11A-11C depict examples of substrate receptacles 904a-904c. The depicted substrate receptacles 904a, 904b, 904c each include an extension 906 that may be used to connect the substrate receptacles 904a, 904b, 904c to features of the drive system, e.g., as depicted above. The substrate receptacle 904a does not include any feature for attaching a disposable cover, as originally described in the context of FIG. 10A. The substrate receptacle 904b includes a hook 910 that projects from an underside of the receptacle 904b, while the substrate receptacle 904c includes a hook 910 that projects from a side of the receptacle 904c. In other examples, pins, buttons, tabs, or other structures may be used for securing a disposable cover over the foam compressive element.

Figure 12:
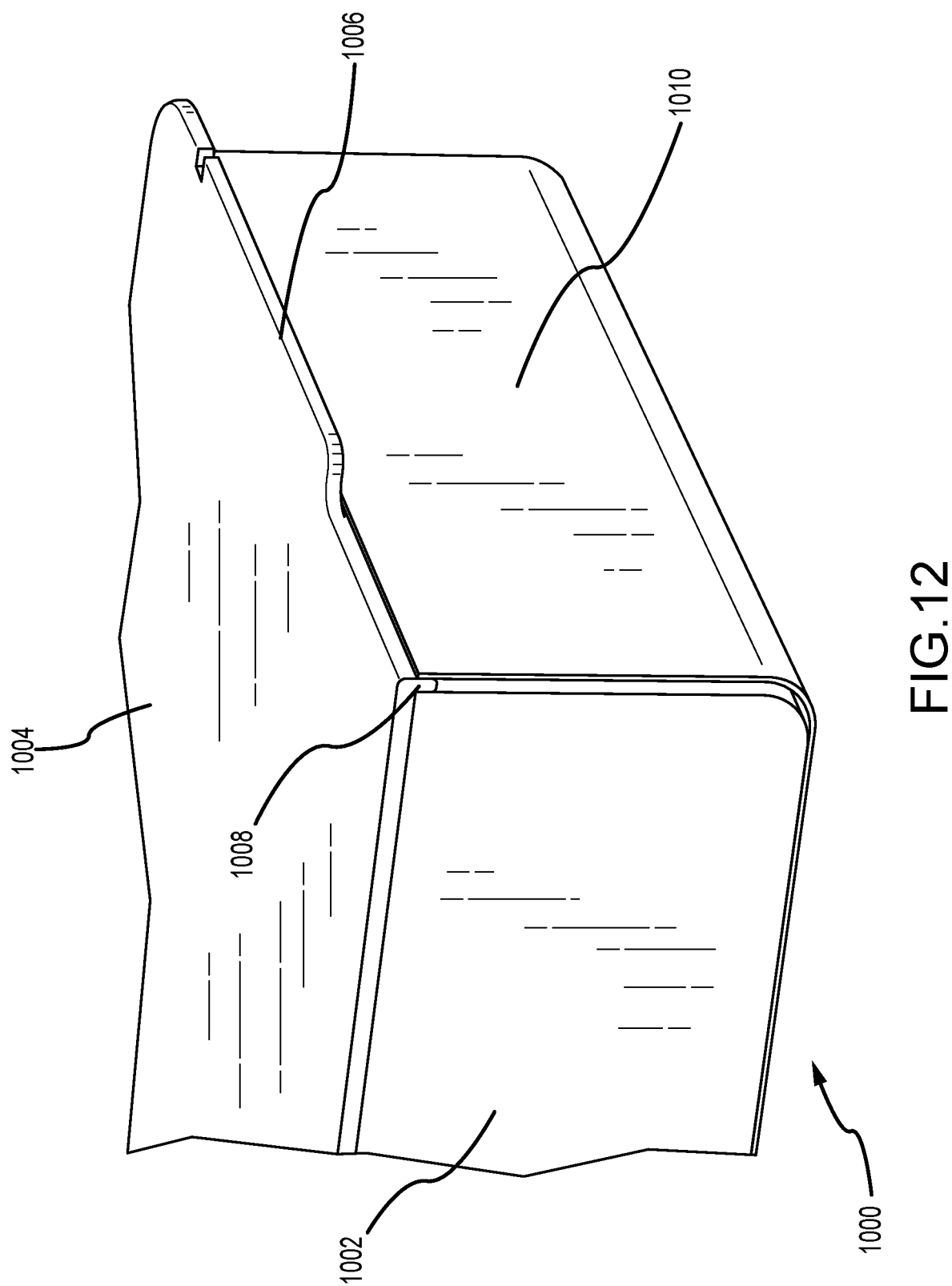
FIG. 12 depicts another example of a breast stabilizing element.

FIG. 12 depicts another configuration of a breast stabilizing element 1000, which includes a foam compressive element 1002 secured to a rigid substrate 1004. The substrate may include one or more edges 1006 extending outward therefrom that are configured for engagement with a substrate receptacle, as described elsewhere herein. Projecting downward from the rigid substrate 1004 is a flange 1008. The flange 1008 may serve multiple purposes. For example, the flange 1008 may act as a guide during insertion of the rigid substrate 1004 into the substrate receptacle. In another example, the flange 1008 may serve as an area of adhesion for a flexible covering 1010 that may be disposed at least partially surrounding the foam compressive element 1002. The flexible covering may be resistant to transmission of moisture or other fluids, or may be decorative, softer than the foam compressive material itself, etc. By not adhering the flexible coving 1010 to the foam compressive element 1002, the foam compressive element 1002 may deform and deflect as designed. Incorporation of the flange 1008 and adhesion of the covering 1010 thereto may help reduce or eliminate small surfaces or interfaces that would require cleaning between different patients.

Figure 13:
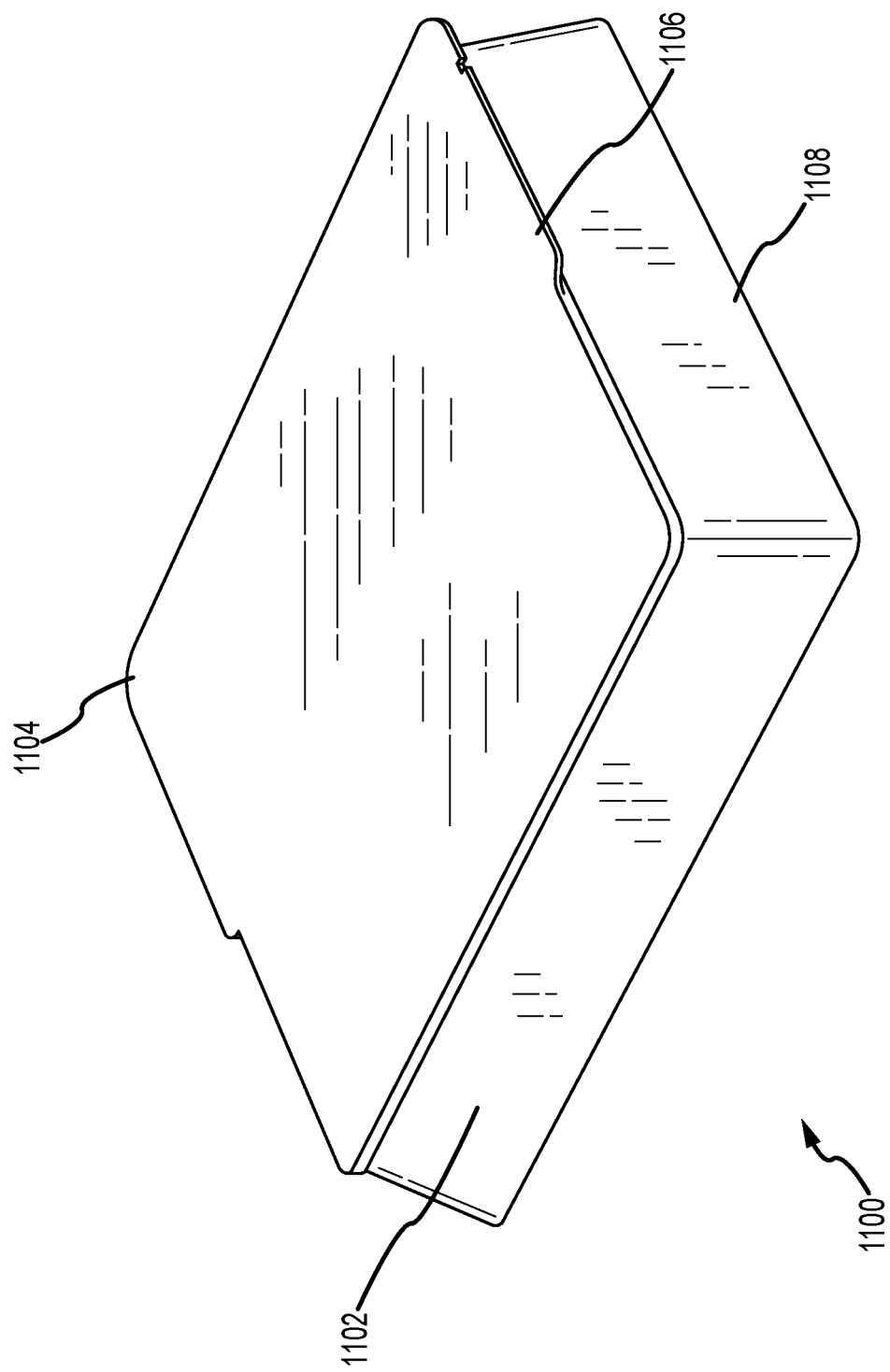
FIG. 13 depicts another example of a breast stabilizing element.

FIG. 13 depicts another configuration of a breast stabilizing element 1100, which includes a foam compressive element 1102 secured to a rigid substrate 1104. The substrate may include one or more edges 1106 extending outward therefrom that are configured for engagement with a substrate receptacle, as described elsewhere herein. Here, the foam compressive element 1102 includes a substantially beveled shaped, extending outward in one or more directions from the rigid substrate 1104. As such, the outer edges 1108 of the foam compressive element 1102 may project further away from the edges 1106 of the rigid substrate 1104. This can help reduce the potential for contact between the rigid substrate 1104 and the patient breast.

Figure 14:
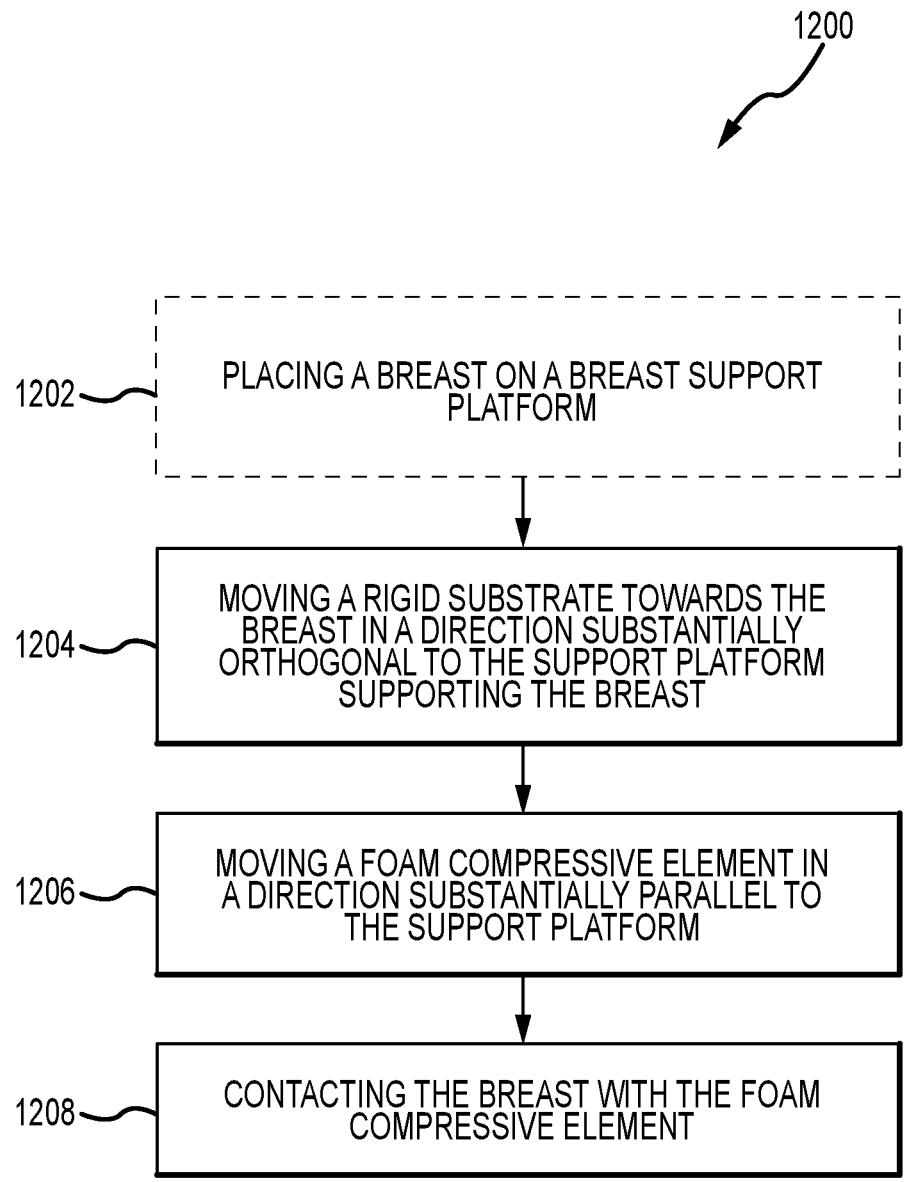
FIG. 14 depicts a method of positioning a breast for x-ray imaging.

FIG. 14 depicts a method 1200 of positioning a breast for x-ray imaging. The method 1200 may begin with optional operation 1202, placing the breast on a support platform, examples of which are depicted herein. Flow continues to operation 1204, moving a rigid substrate towards the breast in a direction substantially orthogonal to the support platform supporting the breast. Operation 1206 contemplates moving a foam compressive element in a direction substantially parallel to the support platform. In examples, moving the rigid substrate, operation 1204, includes a first moving the rigid substrate operation and a second moving the rigid substrate operation. In those examples, moving the foam compressive element, operation 1206, may be performed between the first moving the rigid substrate operation and the second moving the rigid substrate operation.

Various directional movements of foam compressive elements and rigid substrates are described herein. In examples, the direction substantially parallel to the support platform is substantially parallel to the chest wall, while in other examples, the direction substantially parallel to the support platform is substantially orthogonal to the chest wall. In certain examples, moving the foam compressive element in the direction substantially parallel to the support platform includes moving the rigid substrate in the direction substantially parallel to the support platform. Further, as depicted herein, moving the rigid substrate and moving the foam compressive element are each performed via at least one motor. Subsequent to the various movements, operation 1208, contacting the breast with the foam compressive element, is performed, followed by imaging procedures.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of positioning a breast of a patient for x-ray imaging, the method comprising:
   moving at least a portion of a paddle towards the breast in a direction substantially orthogonal to a support platform supporting the breast, wherein the at least a portion of the paddle includes a compression region and a bracket;
   connecting a rigid substrate of a foam element to the bracket of the paddle proximate to the compression region and via a connection system, wherein at least a portion of the rigid substrate is received within a substrate receptable extending from the bracket; and
   contacting the breast with the foam element.

2. The method of claim 1, wherein moving the at least a portion of the paddle comprises a first moving operation of the at least a portion of the paddle and a second moving operation of the paddle, and wherein connecting the foam element to the at least a portion of the paddle is performed between the first moving operation and the second moving operation.

3. The method of claim 1, further comprising placing the breast on the support platform.

4. The method of claim 1, wherein connecting the foam element to the at least a portion of the paddle comprises sliding the foam element in a direction substantially parallel to the support platform.

5. The method of claim 1, further comprising moving the substrate receptacle relative to the bracket once the at least a portion of the rigid substrate is within the substrate receptacle.

6. The method of claim 1, further comprising engaging a pin within the substrate receptacle with the rigid substrate to connect the foam element to the at least a portion of the paddle.

7. The method of claim 1, wherein when the at least a portion of the rigid substrate of the foam element is received within the substrate receptacle, clearance is provided between the rigid substrate and the bracket.

8. The method of claim 1, wherein connecting the foam element to the at least a portion of the paddle comprises aligning the rigid substrate of the foam element with the compression region of the paddle.

9. A paddle for a breast x-ray imaging system, the paddle comprising:
   a bracket configured to couple to the breast x-ray imaging system;
   a compression region extending from the bracket;
   a foam element having a rigid substrate secured thereto; and
   a connection system for removably connecting the foam element to the bracket proximate the compression region, the connection system includes a substrate receptacle extending from the bracket and that couples to at least a portion of the rigid substrate.

10. The paddle of claim 9, wherein a pin is disposed at least partially within the substrate receptacle for engaging the rigid substrate.

11. The paddle of claim 9, wherein the at least a portion of the rigid substrate is slidably received by the substrate receptacle.

12. The paddle of claim 9, wherein the substrate receptacle includes a guide for receiving the rigid substrate.

13. The paddle of claim 9, wherein the substrate receptacle is moveable on the bracket.

14. The paddle of claim 9, wherein the substrate receptacle extends from a mount that couples to the bracket, the rigid substrate having clearance relative to the bracket.

15. The paddle of claim 9, wherein the rigid substrate includes at least one of a flange and an edge.

16. The paddle of claim 9, wherein the rigid substrate is magnetically coupled to the substrate receptacle.

17. The paddle of claim 16, further comprising one or more alignment features on the rigid substrate and the substrate receptacle.

18. A method of positioning a breast of a patient for x-ray imaging, the method comprising:
   moving at least a portion of a paddle towards the breast in a direction substantially orthogonal to a support platform supporting the breast;
   connecting a foam element to the at least a portion of the paddle via a connection system, wherein connecting the foam element to the at least a portion of the paddle comprises magnetically coupling at least a portion of a rigid substrate of the foam element with a substrate receptacle extending from a bracket; and
   contacting the breast with the foam element.

* * * * *